(12) United States Patent
Sobek

(10) Patent No.: US 10,227,631 B2
(45) Date of Patent: *Mar. 12, 2019

(54) COMPOSITION, DEVICE, AND METHOD FOR BIOLOGICAL AIR SAMPLING

(71) Applicant: Edward Sobek, Oak Ridge, TN (US)

(72) Inventor: Edward Sobek, Oak Ridge, TN (US)

( * ) Notice: Subject to any disclaimer, the term of this patent is extended or adjusted under 35 U.S.C. 154(b) by 465 days.

This patent is subject to a terminal disclaimer.

(21) Appl. No.: 14/864,934

(22) Filed: Sep. 25, 2015

(65) Prior Publication Data

US 2016/0032352 A1 Feb. 4, 2016

Related U.S. Application Data

(62) Division of application No. 13/448,058, filed on Apr. 16, 2012, now Pat. No. 9,170,178.

(51) Int. Cl.
| | |
|---|---|
| *B01D 24/00* | (2006.01) |
| *C12Q 1/24* | (2006.01) |
| *G01N 1/22* | (2006.01) |
| *B01D 24/20* | (2006.01) |
| *B01D 46/30* | (2006.01) |
| *B01D 47/04* | (2006.01) |
| *G01N 1/40* | (2006.01) |
| *G01N 1/24* | (2006.01) |

(52) U.S. Cl.
CPC .............. *C12Q 1/24* (2013.01); *B01D 24/00* (2013.01); *B01D 24/205* (2013.01); *B01D 46/30* (2013.01); *B01D 47/04* (2013.01); *G01N 1/22* (2013.01); *G01N 1/2202* (2013.01); *G01N 1/2205* (2013.01); *G01N 1/2214* (2013.01); *G01N 1/2273* (2013.01); *G01N 1/24* (2013.01); *G01N 1/405* (2013.01); *G01N 1/4077* (2013.01); *G01N 2001/2217* (2013.01); *G01N 2001/2223* (2013.01); *G01N 2333/78* (2013.01)

(58) Field of Classification Search
None
See application file for complete search history.

(56) References Cited

U.S. PATENT DOCUMENTS

| | | |
|---|---|---|
| 6,635,684 B2 | 10/2003 | Lai et al. |
| 2002/0161440 A1 | 10/2002 | Son et al. |
| 2006/0073585 A1 | 4/2006 | McDevitt et al. |
| 2008/0149561 A1 | 6/2008 | Chu et al. |
| 2010/0028396 A1 | 2/2010 | Ward et al. |
| 2010/0298788 A1 | 11/2010 | Uematsu |
| 2011/0313383 A1 | 12/2011 | Hofstetter et al. |

OTHER PUBLICATIONS

Nuttleman, Charles R., et al., Attachment of fibronectin to poly(vinyl alcohol) hydrogels promotes NIH3T3 cell adhesion, proliferation, and migration, 2001, J Biomed Mater Res., vol. 57, Ed. 2, pp. 217-223.

*Primary Examiner* — Erik B Crawford
(74) *Attorney, Agent, or Firm* — Luedeka Neely Group, P.C.

(57) ABSTRACT

The present invention generally relates to air sampling of biological compounds. Specifically, the present invention relates to a device and method for sampling the ambient air for detecting microbial propagules, microbial propagules being any spore, vegetative cell, or virion of microbiological origin including all bacteria, fungi, viruses, protozoans, molds, slime molds, chlamydospores, hyphae, and cysts.

10 Claims, 13 Drawing Sheets

Specification includes a Sequence Listing.

COMPOSITION, DEVICE, AND METHOD FOR BIOLOGICAL AIR SAMPLING

This application is a division of co-pending application Ser. No. 13/448,058, filed Apr. 16, 2012, the disclosure of which is herein incorporated by reference.

BACKGROUND OF THE INVENTION

Field of the Invention

The present invention generally relates to air sampling of biological compounds. Specifically, the present invention relates to a composition, device, and method for sampling the ambient air for detecting microbial propagules, microbial propagates being any spore, vegetative cell, or virion of microbiological origin including all bacteria, fungi, viruses, protozoans, molds, slime molds, chlamydospores, hyphae, and cysts. In particular, the present invention discloses a biological compound that can be used for collecting mold spores that allows for the increase of detection accuracy. By using this invention, mold spores can be detected with heretofore unprecedented qualitative and quantitative accuracy when submitted to a biological laboratory for subsequent analysis.

Description of the Related Art

At the present, all air sampling for detecting microbial propagules require extensive sample preparation for capturing a sample, carefully preserving the sample, and subsequently submitting this sample to a biological testing laboratory for later analysis. Further, current capture media are not well suited for the identification of microbial propagules. This is because current adhesive technologies are incompatible with the molecular techniques most suited for identification, for example, DNA. The most important of these properties include the capture and stabilization of cells in situ for molecular manipulation using a wide variety of genetic and protein techniques. Thus, present detection of microbial propagules cannot easily be accomplished with both speed and accuracy. There is therefore a great need in the art for the capture of mold spores from air samples with the subsequent accurate determination, identification, and quantification of the microbial propagules.

Accordingly, there is now, provided with this invention, an improved method and device effectively overcoming the aforementioned difficulties and longstanding problems inherent in current capture matrices. These problems have been solved in a simple, convenient, and highly effective way by which to create a medium for the accurate collection, identification, and quantification of microbial propagules from an on-site air analysis.

The current invention combines purified water, a synthetic polymer and connective tissue proteins. The combination of which comprise a biomixture with novel properties; properties that allow for adhesion and manipulation of microbial propagules. The properties of the biomixture provide advantages not available with current adhesive technology. Compatibility with molecular techniques provides the present biomixture invention with the advantage of precision DNA diagnostics including PCR, QPCR, and MSQPCR. DNA diagnostics are extremely sensitive in their ability to detect and quantify microbial species including identification of pathogenic microbial strains or chimeric mutants. However, the biomixture's properties provide scientist with a tool that goes beyond identification purposes. These include manipulation of cells stabilized in the biomixture. Since connective tissue proteins bind to surface receptors it may be possible to design molecular tools to activate microbial cells or genetically transform cells to produce novel products; a valuable tool for the pharmaceutical and biofuel industries.

SUMMARY OF THE INVENTION

According to one aspect of the invention, a composition for collecting microbial propagules is disclosed. The composition comprises a mixture of a water soluble polymer with water and a connective tissue protein added to the polymer-water mixture for forming a biomixture.

According to another aspect of the invention, a method of collecting microbial propagules is disclosed. The method comprises applying a biomixture to a substrate, wherein the biomixture comprises a mixture of a water soluble polymer, water, and a connective tissue protein and making a fluid connection between the substrate and a vacuum pump for collecting an air sample therethrough.

According to yet another aspect of the invention, a device for air sampling is disclosed. The device comprising a housing and a capture matrix positioned in the housing. The capture matrix has a biomixture therewith and the biomixture comprises a mixture of a water soluble polymer, water, and a connective tissue protein. The device further comprises a vacuum pump attachment for attaching a vacuum pump to the housing for drawing air through the capture matrix.

As will be appreciated by those persons skilled in the art, a major advantage provided by the present invention is to provide a medium for the accurate collection, detection, identification, and quantification of microbial propagules from an on-site air analysis. It is therefore an object of the present invention to provide a biomixture with novel properties; properties that allow for adhesion and manipulation of microbial propagules. It is another object to provide a composition, device, and method for sampling the ambient air for detecting microbial propagules. Additional objects of the present invention will become apparent from the following description.

The method and apparatus of the present invention will be better understood by reference to the following detailed discussion of specific embodiments and the attached figures which illustrate and exemplify such embodiments.

DESCRIPTION OF THE DRAWINGS

A specific embodiment of the present invention will be described with reference to the following drawings, wherein.

DESCRIPTION OF THE PREFERRED EMBODIMENT

The following preferred embodiment, as exemplified by the drawings, is illustrative of the invention and is not intended to limit the invention as encompassed by the claims of this application. A composition, apparatus, and method for on-site biologically testing air samples for microbial propagules, microbial propagules being any spore, vegetative cell, or virion of microbiological origin including all bacteria, fungi, viruses, protozoans, molds, slime molds, chlamydospores, hyphae, and cysts is disclosed herein.

The current invention combines purified water, a synthetic polymer, and a connective tissue protein for forming the biomixture of the present invention. Sterile distilled water is the solvent and the synthetic polymer may typically be polyvinyl alcohol. After the biomixture has been made, it is then applied to a capture medium. The biomixture is made using the following method.

Figure 1:
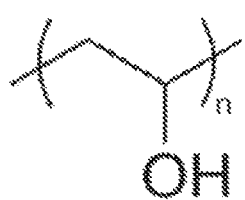
FIG. 1 is a drawing of a polyvinyl alcohol molecule.

Add 5 grams (+/−0.1 gram) of polyvinyl alcohol (PVA) to 1000 milliliters of distilled water. A depiction of the polyvinyl alcohol molecule is shown in FIG. 1. Polyvinyl alcohol (PVOH, PVA, or PVAl) is a water-soluble synthetic polymer used as a constituent of the current invention. Other compounds exist that are similar to PVA and may serve as a base although none have been empirically tested. For example, such, other compounds may be polyvinylpyrrolidone (PVP), also commonly called polyvidone of povidone. (This is a water-soluble polymer made from the monomer N-vinylpyrrolidone). Such other compounds may also be polyvinyl nitrate, polyvinyl acetals, like polyvinyl butyral and polyvinyl formal, or polyvinyl acetate. The PVA may be in the range of about 5% to about 30% of the volume of the biomixture.

Heat the solution to 230° (the melting point of PVA) and stir the solution until all of the polyvinyl alcohol has been dissolved. Typically, a stir plate may be used at 600 revolutions per minute (rpm) at a temperature of 230° C. using this piece of equipment. "Dissolved" is defined as no more PVA granules out of solution or floating free in the solution. Stirring using a stir plate is continuous. If a different method or piece of equipment is used to dissolve the PVA stirring may not and is not required to be continuous.

Allow the 0.5% PVA solution to coot to room temperature, 20-25° C. The solution may stand at room temperature until if has reached room temperature measured by a thermometer. Typically, the temperature may be measured by using an Infrared thermometer. The infrared thermometer is pointed at the solution and the temperature may be immediately relayed to the technician. A standard laboratory thermometer may be used if an infrared thermometer is not available.

Figure 2:
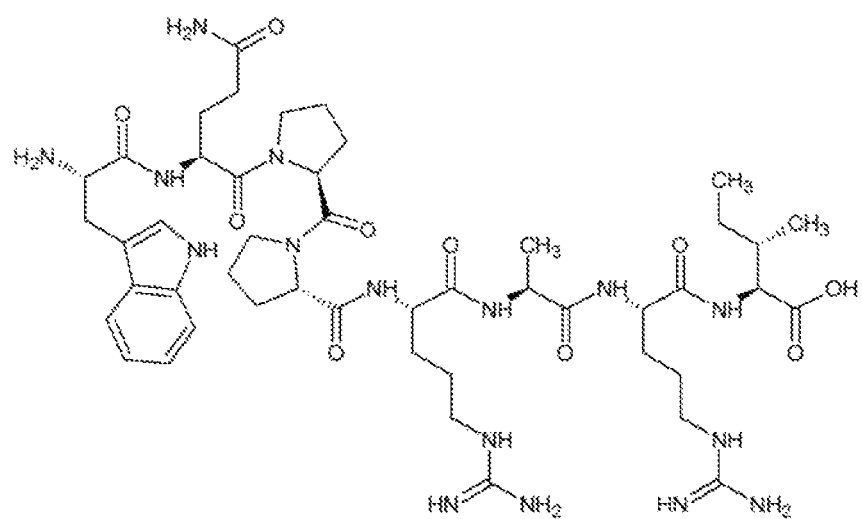
FIG. 2 is a drawing of a molecule of fibronectin.
Figure 3:
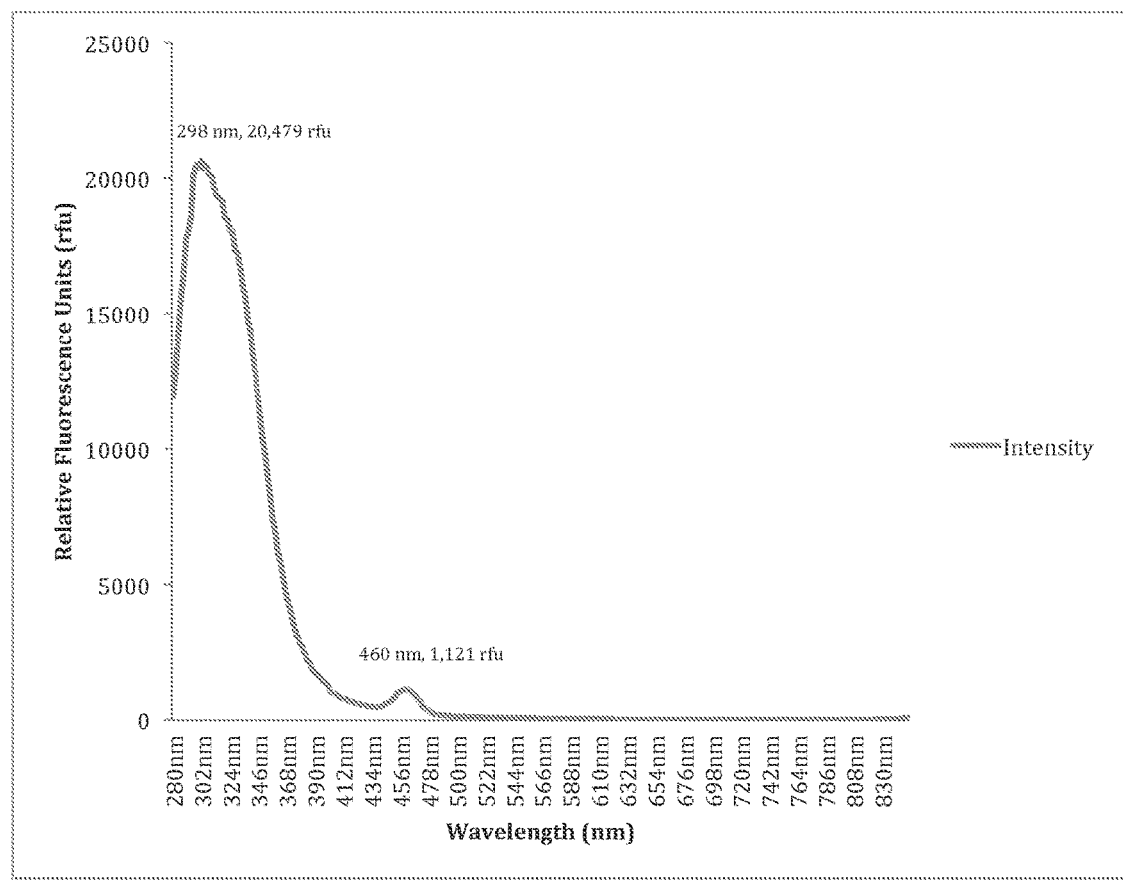
FIG. 3 is a graph depicting fluorescent peaks detected in the biomixture of the present invention.
Figure 4:
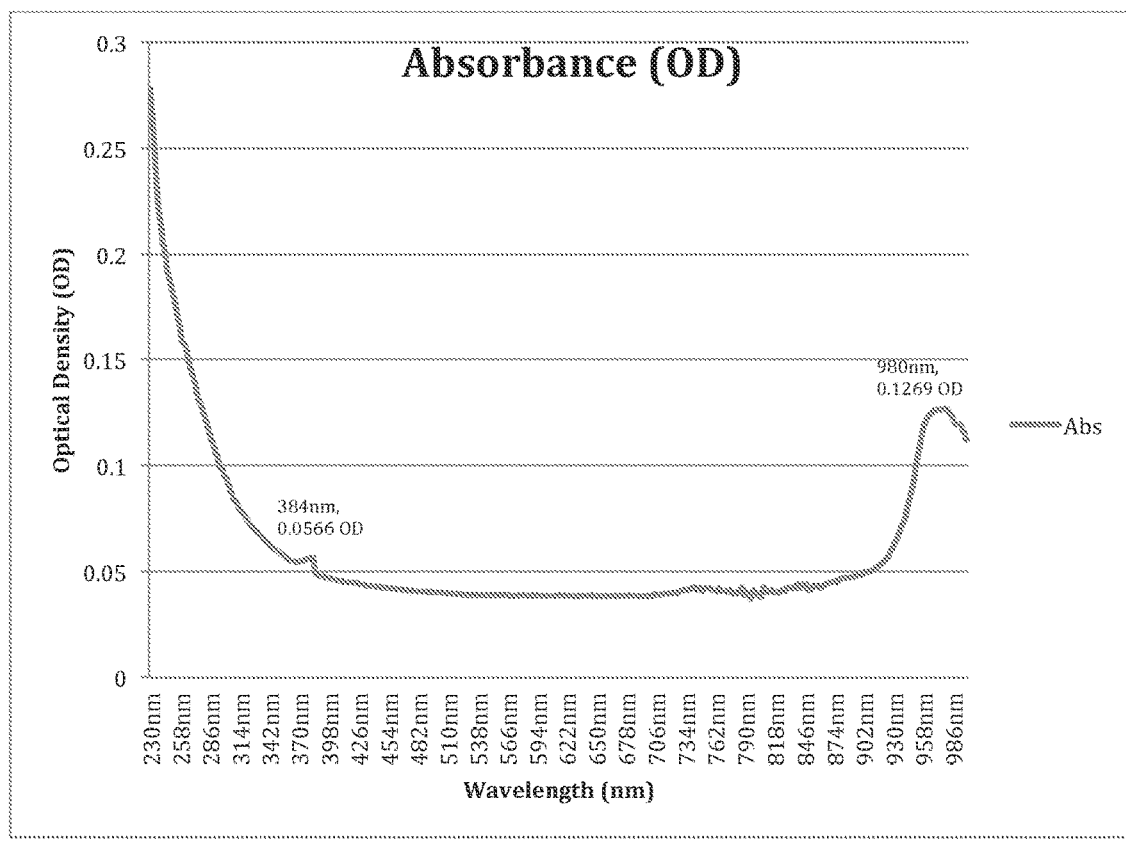
FIG. 4 is a graph depicting absorbance of the biomixture of the present invention as determined by optical density (OD).
Figure 5:
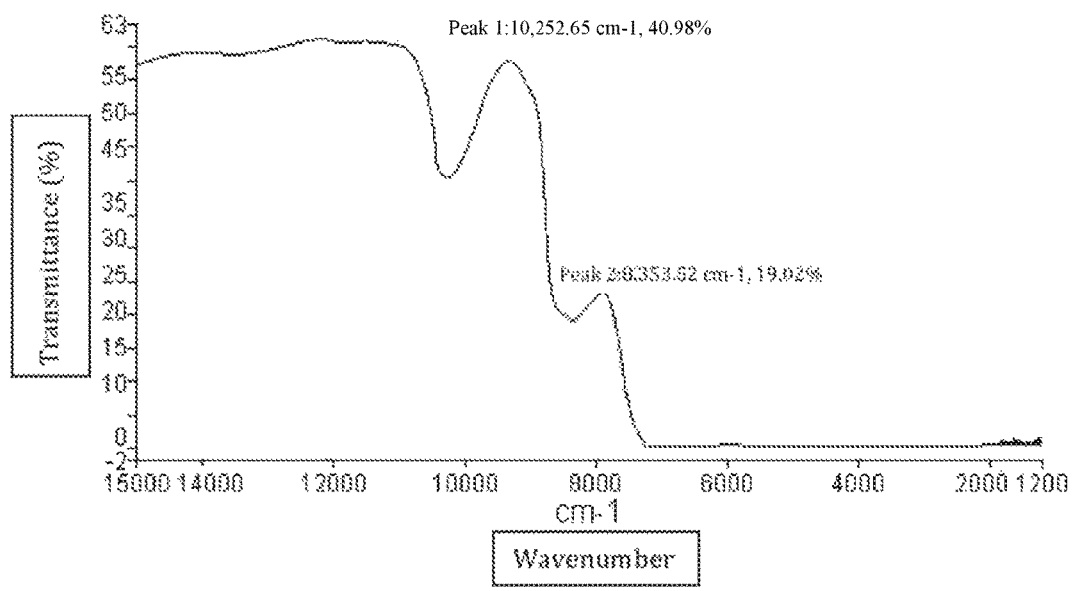
FIG. 5 is a graph depicting Near Infrared Spectrum (NIR) of the biomixture of the present invention.
Figure 6:
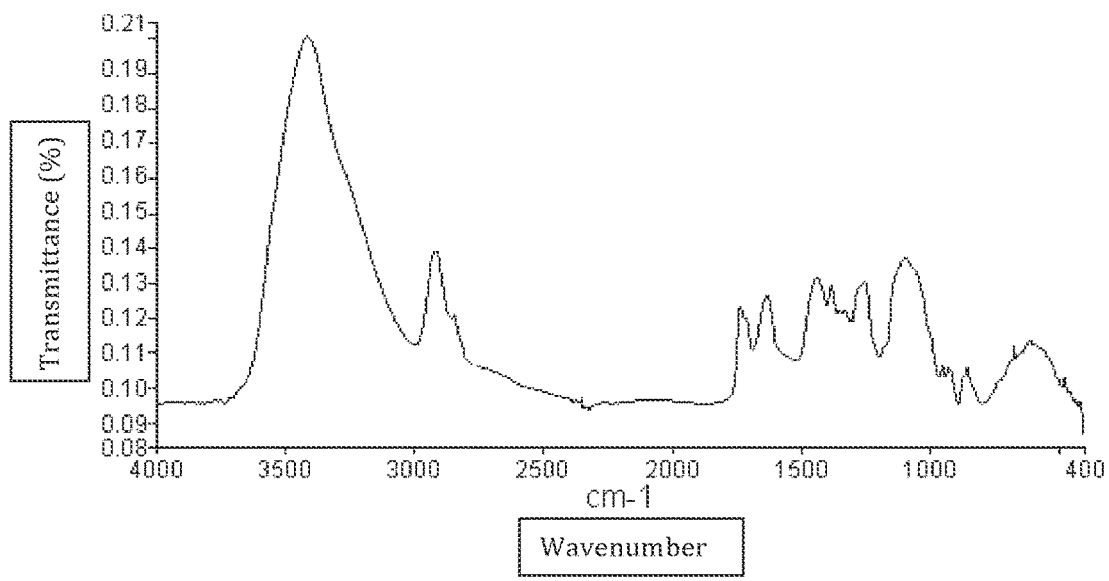
FIG. 6 is a graph depicting the Infrared Spectrum of the biomixture of the present invention.

Add 5 milliliters (+/−0.1 milliliters) of a 1 milligram/milliliter connective tissue protein, for example fibronectin, to the cooled 1000 milliliter PVA solution and stir until dissolved. Do not heat to dissolve. FIG. 2 is a drawing of a molecule of fibronectin. The fibronectin may be in the range of about 5 nanograms/milliliter to 100 nanograms/liter or it can be represented in parts per billion (in the range of from about 0.005 ppb to about 0.1 ppb).

Fibronectin is a high-molecular weight (~440 kDa) glycoprotein of the extracellular matrix and an excellent cellular adhesive. It is crucial for connecting cells within the extracellular matrix. The advantage of using a binding protein in the current invention is realized at the molecular level. Molecular bonds have superior adhesive qualities-that not only maintain cellular structure, but also facilitate cellular function. In effect, molecular bound microbial cells provide fertile ground for in situ molecular manipulation. Applications range from species or strain level identification to precision controlled production of novel pharmaceuticals and biofuels. Biological adhesive proteins that have affinity for microbial surfaces may be substituted for fibronectin. However none have been evaluated empirically. They include but are not limited to the following: vitronectin, collagen, laminin, or hyaluronan. Many similar integrin and surface binding proteins have been identified in the scientific literature.

Them are many different manufacturers of fibronectin, for example, fibronectin may be acquired from Sigma Aldrich. It is typically labeled as a cell culture substrate. Fibronectin may need to be reconstituted with sterile water to achieve the 1 milligram/milliliter concentration prior to mixing the protein with the 0.5% PVA solution. Reconstitution is a standard procedure in a laboratory setting. It is the process of taking a lyophilized (freeze dried, turned into powder form) substrate (molecule, chemical, organism, etc) and adding a solvent (in this case sterile water) to reconstitute the substrate back into liquid form. Substrates are lyophilized by manufacturers to increase their shelf life and reduce shipping costs. Chemicals can be ordered in liquid form at additional costs. A laboratory may or may not need to reconstitute the fibronectin depending on their preference. Typically, reconstitution would comprise adding a solvent (water, alcohol, etc) to the lyophilized substrate.

Add the appropriate amount of sterile water to the amount of lyophilized fibronectin present for forming the biomixture. For example, 1 milliliter (+/−0.1 milliliters) of sterile water to 1 milligram (+/−0.1 milligrams) of lyophilized protein.

Filter sterilize the biomixture solution by a vacuum filter. Typically, the vacuum filter should contain approximately a 0.2 micrometer pore size filter. Filter sterilization is a standard technique used in laboratories. It is the process of removing unwanted components of a solution by vacuum filtration. This is done by using the pressure created by the vacuum to pull the solution through a filter.

The acceptable range of the filter size is 0.01 micrometers. These filters may be ordered from a supplier such as Nalgene which includes the entire filtration apparatus (top compartment that unsterile solution is poured, filter, bottom compartment, where the sterile solution resides after filtration, port where vacuum is attached).

Filter sterilization comprises pouring the solution into the top compartment of the filtration apparatus and turning on the vacuum. The solution will be pulled through the filter into the bottom compartment of the filtration apparatus. Unwanted propagules will be left behind on the filter. The amount of time needed for this step is dependent on the laboratory equipment used. Each laboratory may use their own filtration apparatus and vacuum readily available in their facility. Since the equipment is variable the time required to filter sterilize the solution is variable.

Once the biomixture preparation and sterilization process is complete, aseptically add 200 microliters (+/−0.1 microliters) of the sterile biomixture solution to each sterile 13 millimeter diameter capture medium. "Aseptic" refers to a standard laboratory technique in which the technician pays special care to the sterility of the procedure being performed. This means do not contaminant biomixture or capture medium. To do this wear gloves, work in a sterile environment such as a biological safety cabinet, do not introduce any thing into the procedure that has not deliberately been placed there. This step consists of sterilely transferring the biomixture to the capture medium. Use a pipette (a volumetric instrument used to transfer liquids of an exact volume) capable of transferring 200 microliters of liquid with sterile filter pipette tips.

Allow the capture medium to dry. "Dryness" is defined to be no biomixture residue (wetness) left behind when the capture medium is touched by a sterile gloved hand at room temperature, 20-25° C. The time needed for this step is variable. Humidity in the laboratory will cause the time to dry to increase. Typically, the capture medium may take from 24 hours to 48 hours to completely dry.

The parameters of the biomixture are summarized in the tables below. Table 1 shows a summary of the physical chemistry and Table 2 shows a summary of the viscosity of the biomixture vs. the temperature.

TABLE 1

Summary of Physical Chemistry

| Parameter | Method | Result |
|---|---|---|
| Density | ASTM D891-95 | 0.9994 g/mL |
| Flashpoint | ASTM D56-05 | >96° C. |
| Specific Gravity | ASTM D891-95 | 1.0015 |
| Freezing Point | EP 7.0 | 0° C. |
| pH | Assured Bio Method 168 | 5.21 |

TABLE 2

Summary of Viscosity versus Temperature

| Temperature (Celsius) | Angular Frequency (rad/s) | Viscosity (Pa · s) |
|---|---|---|
| 10 | 62.83 | 2.94E−03 |
| 20 | 62.83 | 2.63E−03 |
| 30 | 62.83 | 2.48E−03 |
| 40 | 62.83 | 2.11E−03 |

Additional physical parameters are shown, for example, in FIGS. 3-6.

Figure 7:
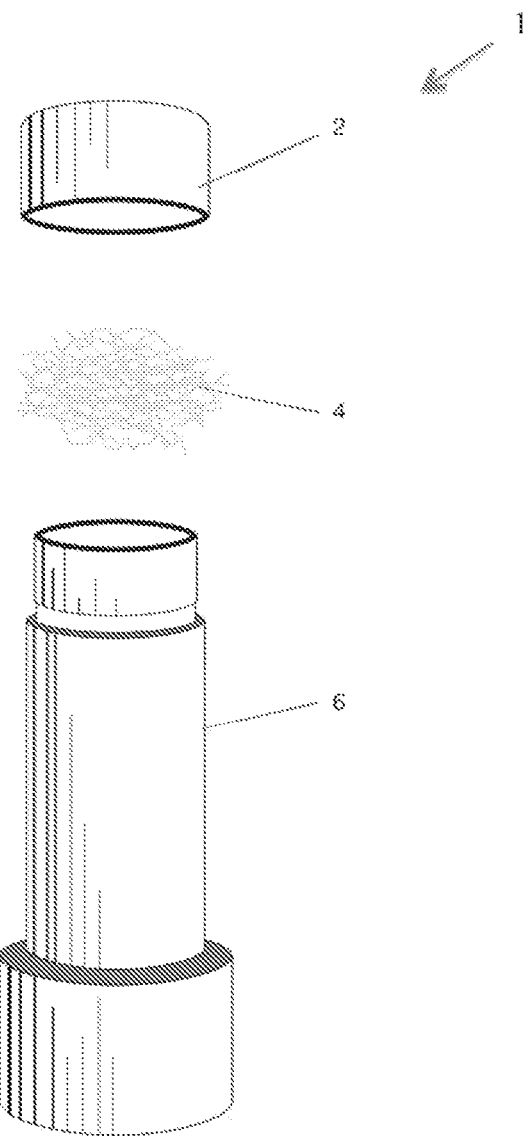
FIG. 7 is an illustration of the capture cassette of the present invention.
Figure 8:
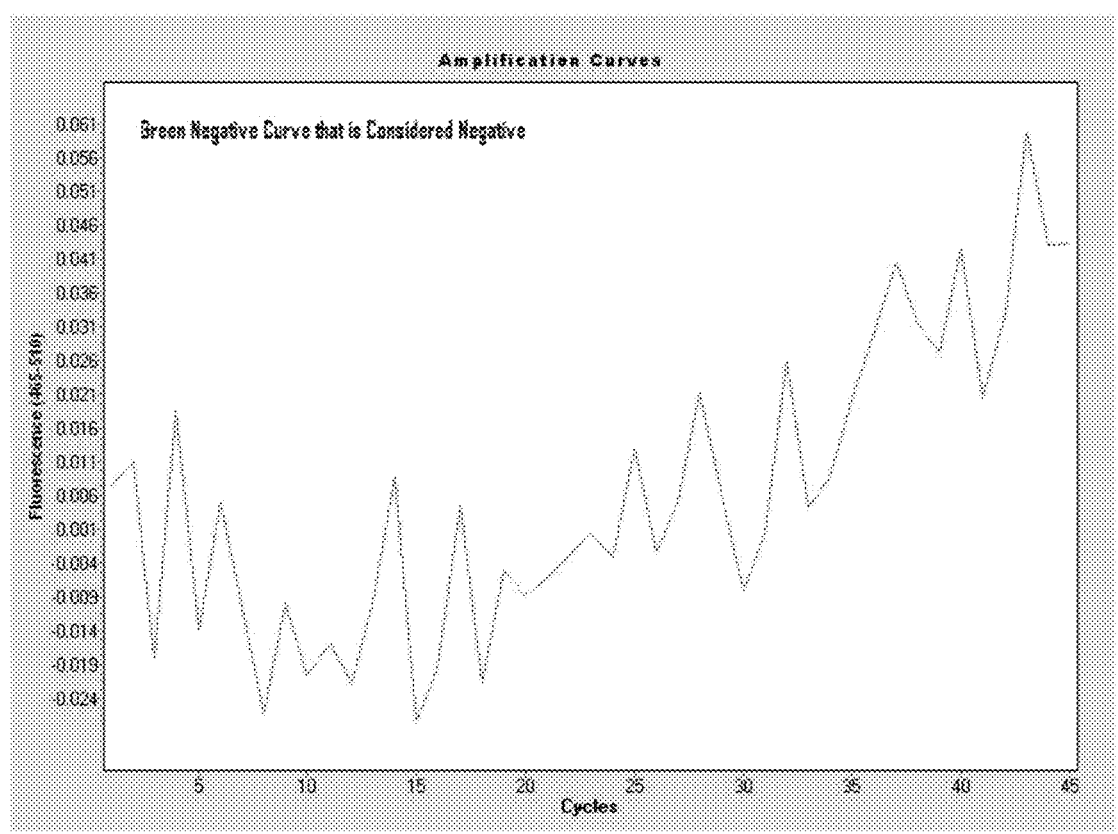
FIG. 8 is a graph depicting a QPCR amplification curve that is considered negative.
Figure 9:
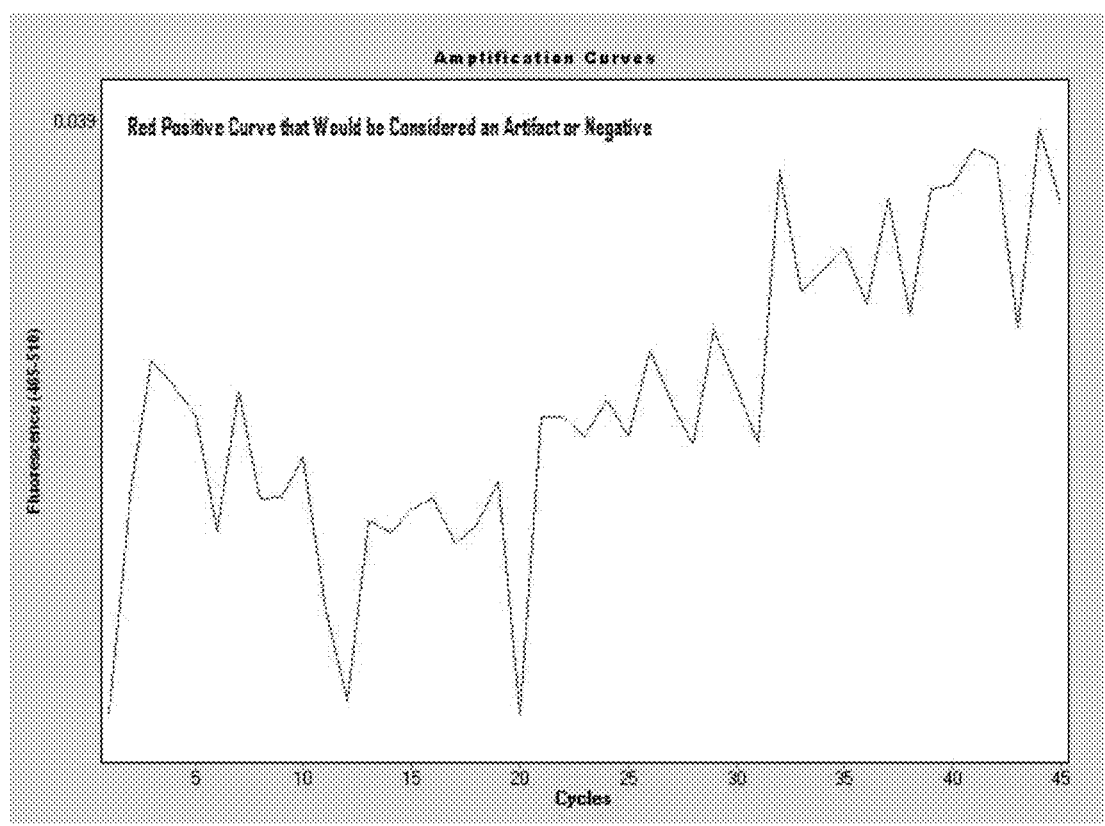
FIG. 9 is a graph depicting a QPCR amplification curve that is considered an artifact or negative.
Figure 10:
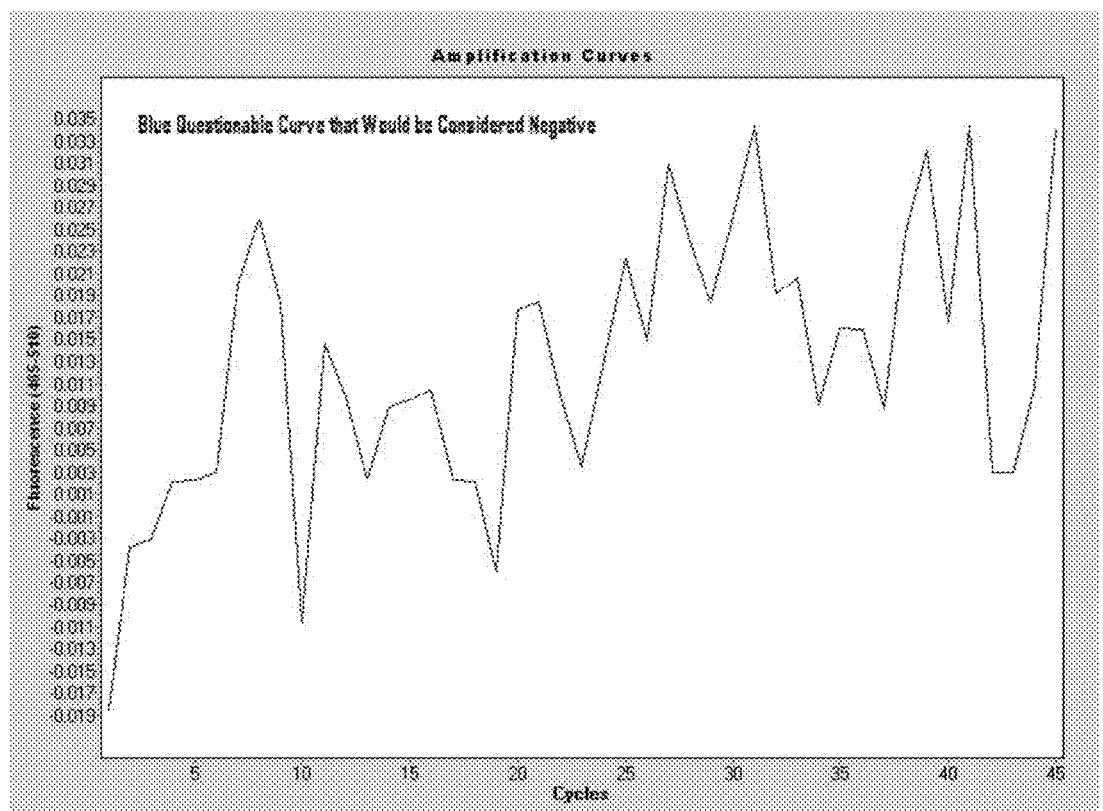
FIG. 10 is a graph depicting a QPCR amplification curve that is considered questionable and negative.
Figure 11:
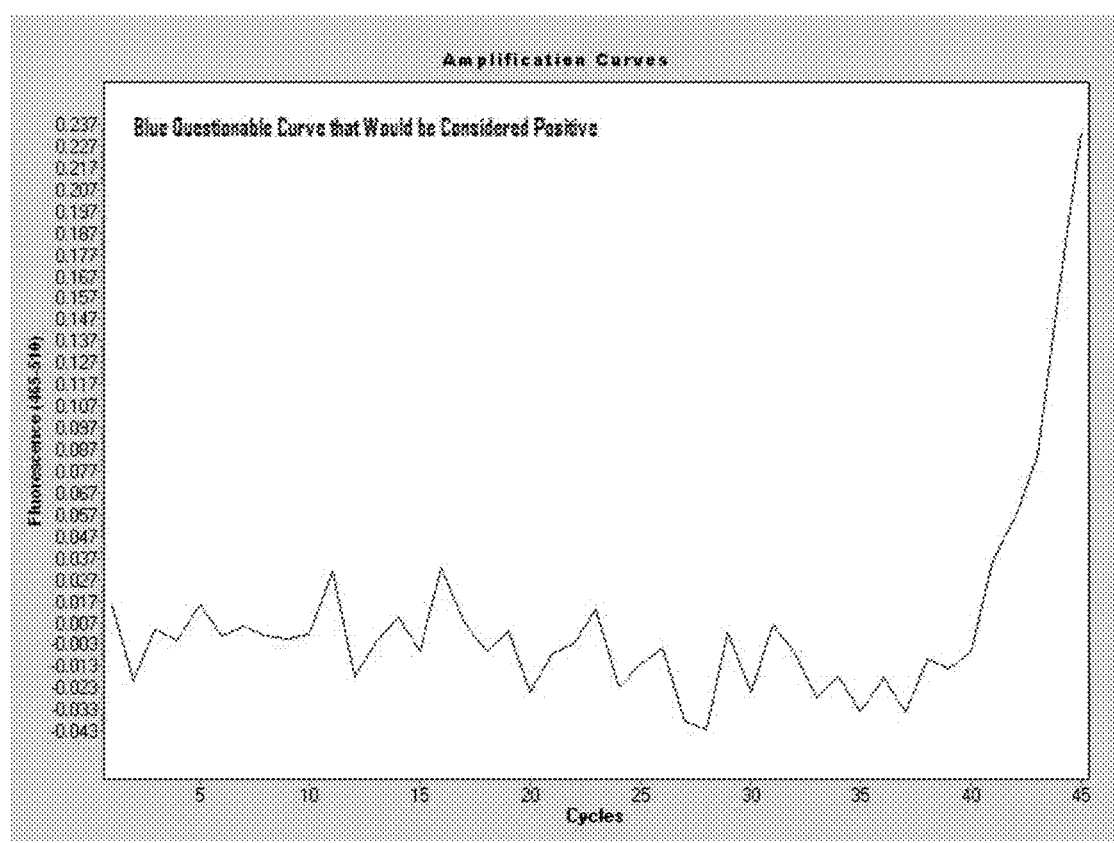
FIG. 11 is a graph depicting a QPCR amplification curve that questionable considered positive.
Figure 12:
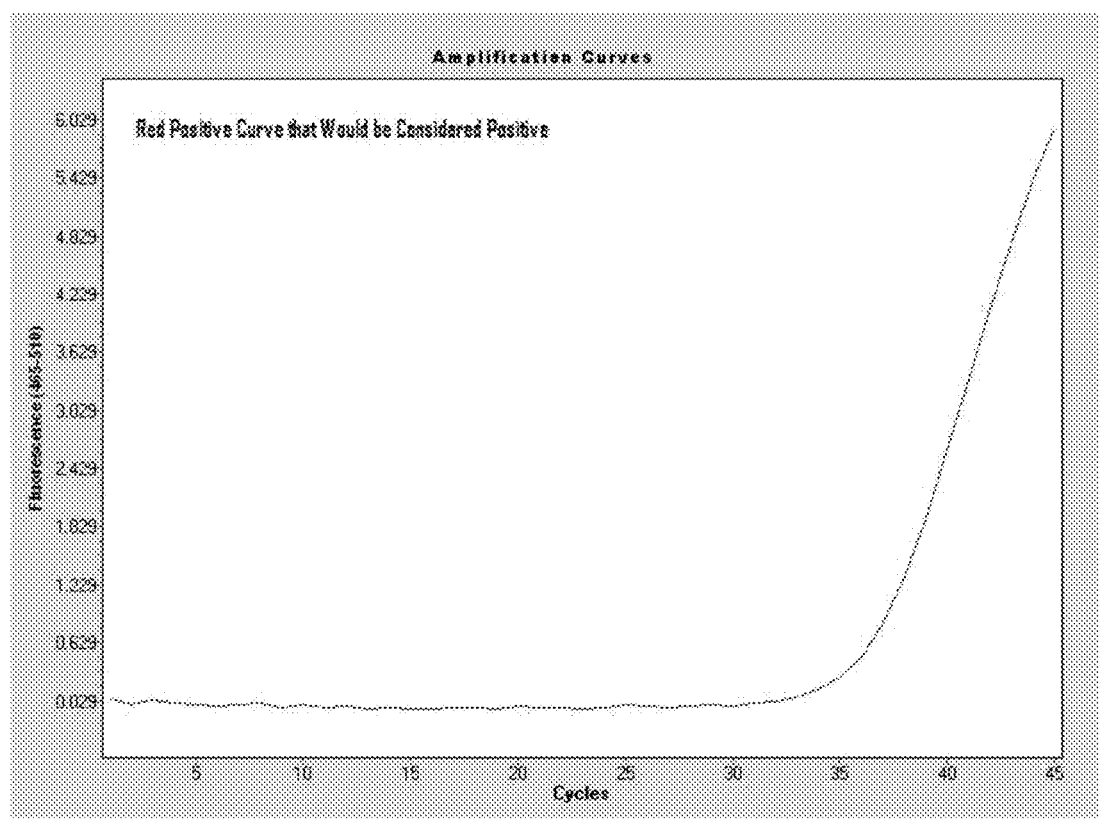
FIG. 12 is a graph depicting a QPCR amplification curve that is considered positive.

FIG. 7 is an illustration of the capture cassette 1 of the present invention. The capture cassette is used for obtaining an on-site air sample. As shown, the capture cassette may comprise a cap 2, a capture matrix 4, and a base 6. The capture cassette may be acquired from AeroLert, LLC, 512 Sussex Ct, Helena, Mont. 59601.

| Item # | AeroLert Part # | Description |
|---|---|---|
| 001 | AERO-H | AeroLert filter and cap assembly. This system only comes as assembly and both parts must be ordered together. |
| 002 | AERO-V | AeroLert vial holder. The system includes a living hinge for securing the completed filter and vial assembly |

The capture matrix 4 typically comprises a densely woven Poly [1,4-cyclohexylene dimethylene terephthalate] (PCT) or similar polyester spun fibers. Alternatives may include a blended PCT with other crystalline and amorphous polymers, natural fibers such as silk or wool, or any of the aforementioned combinations mixed with poly(butylene terephthalate) or poly(ethylene terephthalate). The capture matrix may be acquired from The Warm Company, 5529 186th Place SW, Lynnwood, Wash. 98037. Labeled: Soft and Bright, Needled Poly ester Batting, Reg. No. PA-24653, RN 132520, Federal. Requirements 87.5% Polyester 12.5% Polypropylene. The thickness of the capture matrix may vary from 2 millimeters to 5 millimeters and is coated, as previously described with the biomixture.

The capture matrix is secured to the capture cassette by die cap 2. The cap holds the capture matrix securely in place and seals the crimp cap to the base thereby preventing air leaks and forcing all sampled air to pass through the sampling matrix. The shape and size of the capture matrix may vary depending on application. In this case, the capture matrix is 13 millimeters in diameter, but any diameter and shape is acceptable as long as the capture matrix is secure and all sampled air is directed through the capture medium.

The base 6 includes a connection for a vacuum pump. The connection typically may include a pump adapter connecting the pump and capture cassette when the cassette is used with pumps having ¼" to ¾" outside diameter. The pump adapter may be manufactured by Bel-Art Products Pequannock, N.J. 07440-1999 Catalog Number: 197290000 (Disconnect, PE, Quick, ⅜"-½").

The vacuum pump may be either battery powered or electric and may be supplied by any number of manufacturers. Typically, the vacuum pump may be a rotary pump, for example, AERO-SF-MPS1, manufactured by AeroLert, LLC, 512 Sussex Ct, Helena, Mont. 59601 or manufactured for Aero Tech Laboratories, SN# 099A. The pumping capabilities of the pumps typically used in the indoor air quality industry are measured in terms of flow rate. Empirical data derived from development of the biomixture indicates that the pumps should run at a minimum of 15 liters per minute (L/min) to capture a representative sample of air for polymerase chain reaction analysis (PCR) as per the sampling protocol discussed below.

Higher flow rates than 15 L/min up to 30 L/min do not produce a significant improvement in capture efficiency. Moreover, 15 L/min is often the maximum setting for the battery/electrical powered pump. When the battery/electrical pump is used with the capture cassette, it typically operates at an air flow rate of 15 liters per minute for approximately 10 minutes.

The flow rate of sampled air may vary depending on application. To capture sufficient microbial spores and vegetative cells in a short period of time, such as 5 to 10 minutes, a minimum flow rate of 15 liters per minute is required; however, rates as low as 1 milliliter/minute may be acceptable for certain applications that involve smaller biological particles such as proteins, antibodies, and viruses. Moreover, up to 100 liters per minute flow rate or greater is acceptable if large volumes of air require sampling, such as broad area sampling for biological warfare agents. The key to successful sampling is ensuring correct pump size for a given application and calibration of the chosen pump and knowledge of the movement and behavior of the biological particle in an air stream.

A pump sized correctly for use with the capture cassette must be rated to pull an airstream at a flow rate of at least 15 liters per minute. Most commercial pumps that are capable of pulling 15 liters per minute will be adjustable from a range of 5 liters per minute to 30 liters per minute. These pumps must be fitted with an adjustable rotameter that controls flow rate of the pump. A rotameter is a device that measures the flow rate of a liquid or gas in a closed tube. It belongs to a class of meters called variable area meters, which measure flow rate by allowing the cross-sectional area the fluid travels through to vary, causing some measurable effect. The rotameter must allow for adjustment of the flow rate in 1 liter increments from 5 to 30 liters per minute. Most commercial pumps come with rotameters that meet the flow rate specifications of the pump's flow rate range. The pump specifications should always be checked with the rotameter specifications.

Rotometers are typically used to calibrate the chosen pump. Rotameters are secondary standards and should be calibrated by the user with a primary flow calibrator at regular intervals. Since rotameters are affected by temperature and atmospheric pressure, rotameter calibration should be performed under the conditions of use.

Primary flow calibrators are available from a variety of manufactures, including SKC, Sensidyne, and TSI. All models ensure laboratory accuracy certified by NIST through NVLAP and backed by ISO 17025 accreditation, ANSI Z-540, and NIST Handbook 150. Several options are recommended for rotameters connected to pumps that are capable of a flow rate of 15 liters per minute. They include: SKC Defender model 530 for use with flow rates between 0.3 to 30 liters per minute, SKC Inc. 863 Valley View Road, Eighty Four, Pa. 15330, alternatively, Sensidyne Gilian Challenger for use with flow rates between 1 to 30 liters per minute, 16333 Bay Vista Drive, Clearwater, Fla. 33760, and TSI Incorporated model 4146 for use with flow rates between 0.01 and 20 liters per minute, 500 Cardigan Road, Shoreview, Minn. 55126.

The following is a sampling protocol that may be used for collecting air samples using the capture cassette and used to provide a procedure for the collection of air samples to be processed using polymerase chain reaction (PCR) technology. Further, the following variations of PCR include real-time PCR, also known as quantitative PCR (QPCR), and mold specific QPCR (MSQPCR). Universal precautions should be used when performing any test/procedure or when handling any potentially biohazardous material.

1. Insert the end of the capture cassette to the pump adapter into the ¼ inch tubing.
2. Connect the tubing to the air pump.
3. Set the pump to collect 15 liters/minute.
4. Place the adapter end through the hole on tripod.
5. Adjust the tripod to chest height.
6. Remove the capture cassette from the cassette holder and avoid touching the fibrous end.
7. Connect the capture cassette to the adapter.
8. Collect the air sample for 10 minutes for a total of 150 liters collection volume, (15 liters/minute for 10 minutes)
9. Label the capture cassette by completing a Chain of Custody (COC). It should reflect the Project Name, the Project Date, and the Job Number. Provide a Sample Description, the Capture Cassette Serial Number, Sample Code, and total Volume of air collected for each individual sample. It is important to always indicate the type of testing required (MSQPCR is one such test appropriate for the Capture Cassette). If desired, the conditions such as weather, relative humidity, and temperature may also be reflected on the COC.
10. Insert capture cassette back into the holder. The samples may be shipped using a Next Day Air shipping method to the laboratory, for example, Assured Bio Labs, LLC in Oak Ridge Tenn. at 228 Midway Lane with a zip code of 37830, for analysis.

The following steps are an example of species identification of airborne molds using MSQPCR. Method 163: Prepping Airborne Mold Samples for DNA Extraction for MSQPCR Method 166; Extraction of DNA from Captured Airborne Mold Spores Method 167: Running MSQPCR on Extracted Airborne Mold DNA and Analyzing MSQPCR Results.

The following is the method by which captured spore DNA may be extracted from the capture medium and how the results may be analyzed. These methods should be conducted using aseptic techniques. This includes using a class II biosafety hood to ensure a sterile environment for samples, wearing gloves and a lab coat, and not cross contaminating reagents, samples, or tubes with dirty pipette tips or dirty tweezers. Everything that touches a sample or could possibly come into contact with the sample is to remain sterile.

To prepare the capture matrix for DNA extraction, remove the cassette from the cassette holder. Open the cassette with clean gloved hands by removing seal and snapping off the cap. Flame sterilize a pair of tweezers using 95% ethanol and a flame lamp. Dip the tweezers into ethanol and pass through the flame igniting the ethanol allowing it to burn out on its own. Remove the capture medium by grabbing medium with sterile tweezers and lifting medium off of the cassette base. Place the capture medium into a sterile 2 milliliter bead tube containing 0.3 grams (+/−0.11 grams) glass beads (Sigma Glass beads, acid washed 212-300 micrometer cat# G1277) using the same sterile tweezers. Place the sterile lid onto the bead tube. Label the tube with the corresponding sample number. Sample numbers are typically assigned by the biological lab conducting the analysis upon receipt of sample following the format: Inspector's initials, date of receipt, the number project corresponding to the place in line that project was logged in and the sample number within that project corresponding to the sample number on the chain of custody. This gives each sample a unique ID to use to track samples from receipt of sample to reporting of data.

Add 350 microliters (+/−1 microliter) of the Roche High Pure PCR Template Preparation Kit (Roche Cat# 11796828001) lysis buffer to the bead tube containing the capture medium. Use a 100 microliter-1000 microliter pipette with sterile aerosol filter pipette tips that are Nuclease, DNA, and Endotoxin free (available from VWR). Set the pipette to 350 microliters, draw up the lysis buffer with the pipette and expel the lysis buffer directly into the tube containing the capture medium and the glass beads. Discard the pipette tip in a biological safety receptacle after each sample.

Vortex (mix) reference spore stock (*Geotrichum candidum* at $10^8$ concentration, available from Assured Bio Labs) with a Vortex Genie (available from VWR International) set on 8 (no other speed parameter provided by manufacturer) for 10 seconds. Add 10 microliters (+/−0.1 microliters) to sample using a 0.5 microliter-10 microliter pipette and the same type of sterile aerosol filter pipette tips that are Nuclease, DNA, and Endotoxin free. Set the pipette to 10 microliters, draw up the reference stock and expel directly into the tube containing the lysis buffer, capture medium and glass beads. Rinse any residual spores left on the pipette tip by pipetting up and down 5 times. Discard the pipette tip into a biological safety receptacle and place lid back on sample. Ensure the lid is tight and secure. The reference spore stock is used to ensure the extraction of DNA from fungal spores in each sample is complete and not inhibited by any chemicals collected along with the spores on the capture medium. By placing a known concentration of a reference spore not found in air samples, one is able to rule out the possibility of false negatives. If the reference stock shows there are problems with extraction the sample may need to be reprocessed to rule out the possibilities of false negatives for the spores being analyzed.

Bead beat the bead tube containing the capture medium, lysis buffer, glass beads, and reference spore stock at 6,000 revolutions per minute (rpm) for 14 seconds using, for example, a Roche Magna Lyser (available from Roche). To do this, bead tubes may be placed into the rotor of the Magna Lyser ensuring that all 16 slots are filled with either a sample or a balance of the same weight as the samples. The clamp on the rotor should be tightened to ensure that the samples are secure during the bead beating process. The time and speed should be set and started. The lid will automatically release once samples have finished the bead beating process. Remove sample tubes from the rotor and place them into a sterile tube block. This step uses the Roche High Pure PCR Template Lysis buffer to chemically lyse the spore cells while the Roche Magna Lyser and glass beads manually lyse the mold spores. This combination allows for the rapid release of DNA from mold spores. This process could also be used for other propagules such as bacteria.

Centrifuge the bead tube for 1 minute at 13,200 rpm to collect the sample back into the bottom of the tube. To do this, place the samples into a centrifuge capable of a speed of 13,200 rpm, for example, the eppendorf 5415D. Ensure the rotor is balanced with samples and weighted blanks. For example, two samples of the same weight should be placed directly across from each other in position 1 and 13 to achieve a balanced rotor. Set the time and speed and press start. The lid will automatically release once the centrifuge has finished. Remove the samples from the centrifuge and place back into the same sterile tube block.

Snap off the base of a pre-filter (Zymo-Spin IV cat# C1007) using a clean gloved hand and insert into a sterile 2 milliliter collection tube (provided with the Roche High Pure PCR Template Preparation Kit). Place the 2 milliliter collection tube with the pre-filter into the sterile tube block. Label the tube with the corresponding sample number.

Transfer the capture medium and the supernatant (liquid portion of the bead tube containing the lysis buffer, reference spore stock and released DNA) to pre-filter and place sterile cap onto pre-filter. To do this, use a 100 microliter-1000 microliter pipette set on 400 microliters. One can reuse the same pipette as before as long as sterility has not been compromised. Sterile aerosol filter pipette tips should be changed after each sample. All used pipette tips should be discarded from the pipette into a biological safety receptacle after use. Pipette as much of the liquid from the bead rube into the pre-filter/2 milliliter collection tube apparatus. Next, flame sterilize a pair of tweezers using 95% ethanol and a flame lamp as before. Grasp the collection medium residing in the bead tube with the sterile tweezers and transfer it to the pre-filter, 2 milliliter collection tube and supernatant apparatus. Place the sterile lid on the top ensuring it is tight and secure.

Centrifuge the collection tube containing the pre-filter, capture medium, and supernatant at 7,000 rpm for 1 minute using the eppendorf 5415D centrifuge just as before. Remove the pre-filter, supernatant, capture medium, 2 milliliter collection tube apparatus from the centrifuge and place it back into the sterile tube block. This step filters out any debris such as hair collected on the capture medium from the released spore DNA. It also removes any residual liquid supernatant from the capture medium.

Discard the pre-filter and capture medium by lifting the capped pre-filter off of the 2 milliliter collection tube and placing it into a biological safety receptacle. Retain the flow through or supernatant in the bottom of the 2 milliliter collection tube residing in the tube block. The capture medium can be discarded because the spore DNA has be removed from the medium and released into the supernatant or flow through that is now in the bottom of the 2 milliliter collection tube.

Add 200 microliters (+/−1 microliter) Roche High Pure PCR Template Preparation Kit binding buffer to the filtrate (liquid flow through or supernatant left in the 2 milliliter collection tube from previous step) in the collection tube. Use a 100 microliter-1000 microliter pipette as before set on 200 microliters. Since, the binding buffer has a tendency to form bubbles, one should pay special attention not to form bubbles during this step as cross contamination could occur. Draw up 200 microliters of the binding buffer and expel directly into the 2 milliliter collection tube containing the filtrate. Mix gently with the pipette tip by stirring in a circular motion for 2 seconds. Discard the pipette tip between samples.

Place a sterile high pure filter with attached cap (provided with the Roche High Pure PCR Template Preparation Kit) into a new sterile 2 milliliter collection tube (provided with the Roche High Pure PCR Template Preparation Kit) and set this apparatus into the sterile tube block. Label the top of the high pure filter cap with the corresponding sample number.

Transfer the filtrate with binding buffer to the high pure filter. Use the same pipette as before set at 650 microliters. Draw up the filtrate and expel the filtrate into the high pure filter apparatus and close cap. Discard the pipette tip into a biological safety receptacle.

Centrifuge at 13,200 rpm for 1 minute using the eppendorf 5415D as before. Once centrifugation is complete, remove high pure filter apparatus from the centrifuge and place back into the sterile tube block. These steps bind the DNA to the high pure filter. This allows for further purification of the DNA in downstream steps.

Transfer the high pure filter containing the extracted spore DNA to a new sterile 2 milliliter collection tube (provided with Roche High Pure PCR Template Preparation Kit) by lifting filter off of the 2 milliliter collection tube and placing on the new sterile collection tube. Discard the previous flow through and collection tube, together, into a biological safety receptacle. Place the new high pore filter/2 milliliter collection tube apparatus in the sterile tube block.

Add 500 microliters (+/−1 microliter) of Roche High Pure PCR Template Preparation Kit inhibition buffer to the high pure filter. Use the same 100 microliter-1000 microliter pipette as before. Set the pipette to 500 microliters and draw up the inhibition buffer and expel directly into the high pure filter. Discard the used pipette tip into a biological safety receptacle. Snap the high pore filter cap closed.

Centrifuge at 13,200 rpm for 1 minute using the eppendorf 5415D as before. When centrifugation is complete, remove the high pure filter apparatus and place into the sterile tube block. These steps remove chemicals from the bound DNA that may interfere with the PCR, QPCR, or MSQPCR process.

Transfer the high pure filter containing the bound DNA to a new sterile 2 milliliter collection tube (provided with the Roche High Pure PCR Template Preparation Kit) just as before. Discard the previous flow through and collection tube, together, into a biological safety receptacle.

Add 500 microliters (+/−1 microliter) of Roche High Pure PCR Template Preparation Kit wash buffer to the high pure filter. Use the same 100 microliter-1000 microliter pipette as before set to 500 microliters. Draw up the wash buffer and expel directly into the high pure filter apparatus. Discard the used pipette tip into a biological safety receptacle.

Centrifuge for 1 minute at 13,200 rpm using the eppendorf 5415D as before. When centrifugation is complete, remove the sample from centrifuge and place in the sterile tube block.

Transfer the high pure filter with washed bound DNA to a new sterile 2 milliliter collection tube. Discard the previous flow through and collection tube, together, in a biological safety receptacle.

Add a second 500 microliters (+/−1 microliter) of Roche High Pure PCR Template Preparation Kit wash buffer to the high pure filter. Use the same 100 microliter-1000 microliter pipette as before set at 500 microliters. Draw up the wash buffer and expel directly into the high pure filter apparatus.

Centrifuge for 1 minute at 13,200 rpm using the eppendorf 5415D as before. When centrifugation is complete, remove the sample from centrifuge and place it back into the sterile tube block. These steps further purify the bound DNA leaving behind pure DNA void of any contaminants.

Transfer the high pure filter containing the purified DNA to a new sterile 2 milliliter collection tube (provided with the Roche High Pure PCR Template Preparation Kit). Discard the previous flow through and collection tube, together, into a biological safety receptacle.

Dry the high pure filter containing the purified DNA by centrifuging the high pure filter apparatus for 1 minute at 13,200 rpm using the eppendorf 5415D as before. When, centrifugation is complete, remove the sample from the centrifuge and place it back into the sterile tube block. The purpose of drying the high pure filter is to remove any residual ethanol from the wash steps from the filter that may interfere with the elution (release) of DNA from the filter in the following steps. Drying the filter increases the yield of DNA recovered from the initial sample.

Transfer the dry high pure filter with purified DNA to a new sterile 2 milliliter collection tube. Discard the previous flow through and collection tube, together, into a biological safety receptacle.

Add 100 microliters (+/−0.1 microliter) Roche High Pure PCR Template Preparation Kit elution buffer to the high pure filter. Use a 20 microliter-200 microliter pipette set to 100 microliters. Draw up the elution buffer and expel directly onto the high pure filter. Discard the pipette tip after each sample into a biological safety receptacle.

Centrifuge for 1 minute at 13,200 rpm using the eppendorf 5415D as before. Once centrifugation is complete, remove the high pure filter apparatus from the centrifuge and place back into the sterile tube block.

Retain the flow through and the collection tube. Do not discard anything from the previous step.

Add an additional 100 microliters (+/−0.1 microliter) Roche High Pure PCR Template Preparation Kit elution buffer to the high pure filter. Use the same 20 microliter-200 microliter pipette set to 100 microliters. Draw up the elution buffer and expel directly onto the high pure filter.

Centrifuge for 2 minutes at 13,200 rpm. This will yield 200 microliters of eluted purified DNA. Once centrifugation is complete, remove the sample from the centrifuge and place it back into the sterile tube block. The purpose of these steps is to release the bound DNA from the high pure filter so the DNA can be analyzed.

Discard the high pure filter into a biological safety receptacle. Transfer the eluted spore DNA to a sterile 1.5 milliliter eppendorf snap top tube. Use the 20 microliter-200 microliter pipette set at 200 microliters. Draw up the 200 microliters of eluted DNA and expel it into the sterile tube. Close the cap and label the top of the tube with the appropriate sample number. The spore DNA is now ready for molecular analysis.

Using the eppendorf epMotion 5075, load a 384 well polymerase chain reaction (PCR) plate (available from Roche) with the master mixes (for the species of mold being analyzed) comprised of Roche LightCycler 480 Probes Master cat#04707494001 and Primer and Probes made by IDT and Applied Biosystems. The recipe for the master mixes is found below (section 00139). For the MSQPCR analysis, 37 fungal species' master mixes will be added for analysis. For the 10 microliter reaction, add 7.5 microliters (+/−0.1 microliter) of each species' master mix to 37 wells of the PCR plate. One master mix type per well.

Using the eppendorf epMotion 5075, load the spore DNA to each of the 37 wells of the PCR plate. For the 1.0 microliter reaction add 2.5 microliters (+/−0.1 microliters) of spore DNA. In these steps, the eppendorf epMotion is preprogrammed by the laboratory using the eppendorf software to transfer master mix (7.5 microliters) and DNA (2.5 microliters) into the PCR plate for the exact number of samples selected. For example, for one sample the epMotion is programmed to place each of the 37 mold master mix types into 37 different wells in sequential order. It will then go back and add the DNA from that sample to each of the same 37 wells. For a 384 well plate 10 MSQPCR samples can be processed at one time. 10 samples with 37 different species assays will fill 370 wells of the 384 well plate leaving only 14 wells empty, high throughput.

Seal the PCR plate with sealing film (available from Roche) by pealing the backing from the sealing film and placing directly onto the surface of the PCR plate. Use the provided sealing tool to smooth the seal into place. Centrifuge the plate for 2 minutes at 1,500 rpm using a swinging bucket centrifuge (available font Forma Scientific, Inc).

Place the PCR plate into a real-time PCR machine such as the Roche LightCycler 480 II and start cycles.

The cycle parameters are as follows: 3 Programs which are programmed into the Run Protocol of the Roche machine: Detection format Mono Color Hydrolysis Probe/ UPL Probe Filter FAM (465-510), 384 well block. Reaction Volume—10 microliters.

1. Activation of Taq Polymerase: 1 cycle—Target 95° C.—No Acquisition of Data—Hold for 5 minutes—Ramp Rate 4.8° C./second.

2. Amplification of DNA: 45 cycles—$1^{st}$ Target 95° C.—No Acquisition of Data—Hold for 10 seconds—Ramp Rate 4.8° C./second, $2^{nd}$ Target 60° C.—Single Acquisition of Data in Quantification Mode—Hold for 30 seconds—Ramp Rate 2.5° C./second. Cycle through these two target temperatures for 45 cycles acquiring 45 data points per well on the PCR plate.

3. Cooling of the LightCycler block and PCR plate—1 cycle—Target 40° C.—No Acquisition of Data—Hold for 30 seconds—Ramp Rate 2.5° C./second.

After the cycles are complete, analyze the curves using the real-time PCR machine's software for absolute quantification set on high sensitivity. The software uses the $2^{nd}$ derivative max algorithm of the QPCR amplification curves to analyze the data.

Manually go through each positive curve to decide if the curve, indicating spore DNA present, is in fact a real curve and not an artifact of the machine. The Roche LightCycler software color codes the curves: green are negative, red are positive, and blue are questionable. The curves illustrated in FIGS. 8-12 indicate how to identify each curve type.

Once all of the artifacts and negative blue curves have been deleted, the crossing points (CPs) or crossing threshold points (CTs) need to be exported from the real-time PCR machine. This is the value assigned to each curve by the Roche LightCycler software. It is equal to the point where the slope increases enough to be considered above the background threshold of fluorescence detected by the optics of the machine. Export these values to a spreadsheet. Check to make sure the curve for the reference stock came up within the acceptable range indicating DNA extraction was complete with no inhibition for each sample. For a spore stock at a $10^8$ concentration this CP value should be between 18-22.

Once the data has been quality controlled, the number of spores per cubic meter of air can be calculated. To do this, the amount of liters of air that passed through the capture medium needs to be known. This can be found on the chain of custody form sent in with the sample.

Calculate the spore concentration of each positive curve based on the total volume of air collected using the following equations:

$$10^{((CP-b/m))} = \text{spore concentration on capture medium}$$

Where CP is equal to the crossing point or crossing threshold point of each spore species' positive curve exported from the real-time PCR machine.

b is equal to the y-intercept of each spore species' calibration curve or standard curve.

m is equal to the slope of each spore species' calibration curve or standard curve.

Calibration curves or standard curves values should be completed as part of quality control measures prior to analyzing samples for the assay in question.

Once the spore concentration on the capture medium (SCCM) has been calculated, the spore concentration per cubic meter of air (SCMA) needs to be calculated. The SCMA is calculated with respect to the analytical sensitivity. The analytical sensitivity is found using the collection volume, 1,000/Collection Volume in Liters of Air=Analytical Sensitivity. This is the standard equation to calculate analytical sensitivity for air samples. Multiply the analytical sensitivity by the SCCM to get the SCMA.

Once the exported data has been processed using the previous equations, the analysis of spores present per cubic meter of air collected on capture medium is complete. Report results accordingly. The spreadsheet used includes macros that automatically use the previous equations to calculate and report results by imputing the exported CPs for the MSQPCR analysis from the Roche LightCycler and running the macro.

The master mixes are now described for detecting the captured spore DNA from the capture medium. Species detected by the MSQPCR panel and their sequence of primers and probes used for detection ordered from either IDT or Applied Biosystems are below. Lower case letters denote intentional mismatches with target sequences. Probes labeled with MGB may be ordered from Applied Biosystems. Probe concentrations are 80 nM and primer concentrations are 1000 nM.

*Acremonium strictum*

```
Forward Primer:
5'-CAA CCC ATT GTG AAC TTA CCA AAC

Reverse Primer:
5'-CGC CCC TCA GAG AAA TAC GAT T

Probe:
6FAM-5'-TCA GCG CGC GGT GGC CTC-BHQ
```

*Alternaria alternata*

```
Forward Primer:
5'-GGC GGG CTG GAA CCT C

Reverse Primer:
5'-GCA ATT ACA AAA GGT TTA TGT TTG TCG TA

Probe:
6FAM-5'-TTA CAG CCT TGC TGA ATT ATT CAC CCT TGT CTT T-BHQ
```

Assay Anigr: This assay detects more than one species of mold: *Aspergillus niger, Aspergillus awamori, Aspergillus foetidus, Aspergillus phoenicis*

```
Forward Primer:
5'-GCC GGA GAC CCC AAC AC

Reverse Primer:
5'-TGT TGA AAG TTT TAA CTG ATT GCA TT

Probe:
6FAM-5'-AAT CAA CTC AGA CTG CAC GCT TTC AGA CAG-BHQ
```

Assay Aflav: This assay detects more than one species of mold: *Aspergillus flavus* and *Aspergillus oryzae*

```
Forward Primer:
5'-CGA GTG TAG GGT TCC TAG CGA

Reverse Primer:
5'-CCG GCG GCC ATG AAT

Probe:
6FAM-5'-TCC CAC CCG TGT TTA CTG TAC CTT AGT TGC T-BHQ
```

Assay Afumi: This assay detects more than one species of mold: *Aspergillus fumigatus* and *Neosartorya fischeri*

```
Forward Primer:
5'-GCC CGC CGT TTC GAC

Reverse Primer:
5'-CCG TTG TTG AAA GTT TTA ACT GAT TAC

Probe:
6FAM-5'-CCC GCC GAA GAC CCC AAC ATG-BHQ
```

Assay Aochrl: This assay detects more than one species of mold: *Aspergillus ochraceus* and *Aspergillus ostianus*

```
Forward Primer:
5'-AAC CTC CCA CCC GTG TAT ACC
```

Reverse Primer:
5'-CCG GCG AGC GCT GTG

Probe:
6FAM-5'-ACC TTG TTG CTT CGG CGA GCC C-BHQ

*Aspergillus penicillioides*

Forward Primer:
5'-CGC CGG AGA CCT CAA CC

Reverse Primer:
5'-TCC GTT GTT GAA AGT TTT ACC GA

Probe:
6FAM-5'-TGA ACA CTG TCT GAA GGT TGC AGT CTG AGT ATG-BHQ

Assay Arest: This assay detects more than one species of mold: *Aspergillus restricus, Aspergillus caesillus,* and *Aspergillus conicus*

Forward Primer:
5'-GGG CCC GCC TTC AT

Reverse Primer:
5'-GTT GTT GAA AGT TTT AAC GAT TTT TCT

Probe:
6FAM-5'-CCC GCC GGA GAC TCC AAC ATT G-BHQ

*Aspergillus sclerotiorum*

Forward Primer:
5'-ATT ACT GAG TGA GGG TCC CTC G

Reverse Primer:
5'-CCT AGG GAG GGG GGT TTG A

Probe:
6FAM-5'-CCC GCC GAA GCA ACA AGG TAC G-BHQ

*Aspergillus sydowii*

Forward Primer:
5'-CAA CCT CCC ACC CGA GAA

Reverse Primer:
5'-CCA TTG TTG AAA GTT TGA ACT GAT cTT A

Probe:
6FAM-5'-AGA CTG CAT CAC TCT CAG GCA TGA AGT TCA G-BHQ

*Aspergillus unguis*

Forward Primer:
5'-CAA CCT CCC ACC CTT GAA TAC T

Reverse Primer:
5'-TCA CTC TCA GGC ATG AAG TTC AG

Probe:
6FAM-5'-CAC TGT TGC TTC GGC GAG GAG CC-BHQ

*Aspergillus ustus*

Forward Primer:
5'-AAG GAT CAT TAC CGA GTG CAt GT

Reverse Primer:
5'-GCC GAA GCA ACG TTG GTC

Probe:
6FAM-5'-CCC CCG GGC AGG CCT AAC C-BHQ

*Aspergillus versicolor*

Forward Primer:
5'-CGG CGG GGA GCC CT

Reverse Primer:
5'-CCA TTG TTG AAA GTT TGA ACT GAT cTT A

Probe:
6FAM-5'-AGA CTG CAT CAC TCT CAG GCA TGA AGT TCA G-BHQ

*Aureobasidium pullulans*

Forward Primer:
5'-GAT CAT TAA AGA GTA AGG GTG CTC A

Reverse Primer:
5'-GCT CGC CTG GGA CGA ATC

Probe:
6FAM-5'-CGC CCG ACC TCC AAC CCT TTG-BHQ

*Chaetomium globosum*

Forward Primer:
5'-CCG CAG GCC CTG AAA AG

Reverse Primer:
5'-CGC GGC GCG ACC A

Probe:
6FAM-5'-AGA TGT ATG CTA CTA CGC TCG GTG CGA CAG-BHQ

*Cladosporium cladosporioides* svar. 1

Forward Primer:
5'-CAT TAC AAG TGA CCC CGG TCT AAC

Reverse Primer:
5'-CCC CGG AGG CAA CAG AG

Probe:
6FAM-5'-CCG GGA TGT TCA TAA CCC TTT GTT GTC C-BHQ

*Cladosporium cladosporiodes,* svar. 2

Forward Primer:
5'-TAC AAG TGA CCC CGG CTA CG

Reverse Primer:
5'-CCC CGG AGG CAA CAG AG

Probe:
6FAM-5'-CCG GGA TGT TCA TAA CCC TTT GTT GTC C-BHQ

*Cladosporium herbarum*

Forward Primer:
5'-AAG AAC GCC CGG GCT T

Reverse Primer:
5'-CGC AAG AGT TTG AAG TGT CCA C

-continued

Probe:
6FAM-5'-CTG GTT ATT CAT AAC CCT TTG TTG TCC GAC TCT G-BHQ

*Cladosporium sphaerospermum*

Forward Primer:
5'-ACC GGC TGG GTC TTT CG

Reverse Primer:
5'-GGG GTT GTT TTA CGG CGT G

Probe:
6FAM-5'-CCC GCG GCA CCC TTT AGC GA-BHQ

Assay Earnst: This assay detects more than one species of mold: *eurotium (Aspergillus) amstelodami, Eurotium (Aspergillus) chevalieri, Eurotium (Aspergillus) herbariorum, Eurotium (Aspergillus) rubrum, Eurotium (Aspergillus) repens*

Forward Primer:
5'-GTG GCG GCA CCA TGT CT

Reverse Primer:
5'-CTG GTT AAA AAG ATT GGT TGC GA

Probe:
6FAM-5'-CAG CTG GAC CTA CGG GAG CGG G-BHQ

*Epicoccum nigrum*

Forward Primer:
5'-TTG TAG ACT TCG GTC TGC TAC CTC TT

Reverse Primer:
5'-TGC AAC TGC AAA GGG TTT GAA T

Probe:
6FAM-5'-CAT GTC TTT TGA GTA CCT TCG TTT CCT CGG C-BHQ

Assay Muc1: This assay detects more than one species of mold: *Mucor amphibiorum, Mucor circinelloides, Mucor hiemalis, Mucor indicus, Mucor mucedo, Mucor racemosus, Mucor ramosissimus, Rhizopus azygosporus, Rhizopus homothalicus, Rhizopus microspores, Rhizopus oligosporus, Rhizopus oryzae*

Forward Primer:
5'-CAC CGC CCG TCG CTA C

Reverse Primer:
5'-CCT AGT TTG CCA TAG TTC TCA GCA G

Probe:
6FAM-5'-CCG ATT GAA TGG TTA TAG TGA GCA TAT GGG ATC-BHQ

*Paecilomyces variotii*

Forward Primer:
5'-CGA AGA CCC CTG GAA CG

Reverse Primer:
5'-GTT GTT GAA AGT TTT AAT TGA TTG ATT GT

Probe:
6FAM-5'-CTC AGA CGG CAA CCT TCC AGG CA-BHQ

Assay PenGrp2: This assay detects more than one species of mold: *Penicillium crustosum, Penicillium camemberti, Penicillium commune, Penicillium echinulatum, Penicillium solitum*

Forward Primer:
5'-CGG GCC CGC CTT AAC

Reverse Primer:
5'-GAA AGT TTT AAA TAA TTT ATA TTT TCA CTC AGA GTT

Probe:
6FAM-5'-CGC GCC CGC CGA AGA CA-BHQ

Assay Pbrev: This assay detects more than one species of mold: *Penicillium brevicompactum* and *Penicillium stoloniferum*

Forward Primer:
5'-GGC GAG CCT GCC TTT TG

Reverse Primer:
5'-GAT CCG TTG TTG AAA GTT TTA AAT AAT TTA TA

Probe:
6FAM-5'-CTC GCC GAA GAC ACC TTA GAA CTC TGT CTG A-BHQ

*Penicillium chrysogenum, svar. 2*

Forward Primer:
5'-GCC TGT CCG AGC GTC ACT T

Reverse Primer:
5'-CCC CCG GGA TCG GAG

Probe:
6FAM-5'-CCA ACA CAC AAG CCG TGC TTG AGG-BHQ

*Penicillium corylophilum*

Forward Primer:
5'-GTC CAA CCT CCC ACC CA

Reverse Primer:
5'-GCT CAG ACT GCA ATC TTC AGA CTG T

Probe:
6FAM-5'-CTG CCC TCT GGC CCG CG-BHQ

*Penicillium purpurogenum*

Forward Primer:
5'-AGG ATC ATT ACT GAG TGC GGA

Reverse Primer:
5'-GCC AAA GCA ACA GGG TAT TC

Probe:
6FAM-5'-CCC TCG CGG GTC AAC CT CC-BHQ

*Penicillium variabile*

Forward Primer:
5'-TTA CCG AGT GCG GGT TCt AA

Reverse Primer:
5'-CGA GGC AAC GCG GTA AC

Probe:
MGB-6FAM-5'-CCA ACC TCC CAC CCG TG-BHQ

Assay Pspin2: this assay detects more than one species of mold: *Penicillium glabrum, Penicillium lividum, Penicillium purpurescens, Penicillium spinulosum, Penicillium thomii*

```
Forward Primer:
5'-CAT TAC TGA GTG AGG GCC CTC T

Reverse Primer:
5'-CGT GAG GCG GGa GCA

Probe:
MGB-6FAM-5'-CCA ACC TCC CAC CCG TG-BHQ
```

*Rhizopus stolonifer*

```
Forward Primer:
5'-CAC CGC CCG TCG CTA C

Reverse Primer:
5'-GCT TAG TTT GCC ATA GTT CTC TAA CAA

Probe:
6FAM-5'-CCG ATT GAA TGG TTA TAG TGA GCA TAT GGG
ATC-BHQ
```

Assay SCbrv: This assay detects more than one species of mold: *Scopulariopsis brevicaulis,* and *Scopulariopsis fusca*

```
Forward Primer:
5'-CCC CTG CGT AGT AGA TCC TAC AT

Reverse Primer:
5'-TCC GAG GTC AAA CCA TGA AAT A

Probe:
6FAM-5'-TCG CAT CGG GTC CCG GCG-BHQ
```

*Scopulariopsis chartarum*

```
Forward Primer:
5'-CCC CCT GCG TAG TAG TAA AGC

Reverse Primer:
5'-TCC GAG GTC AAA CCA TCA AG

Probe:
6FAM-5'-TCG CAT CGG GTC CCG GCG-BHQ
```

*Stachybotrys chartarum*

```
Forward Primer:
5'-TCC CAA ACC CTT ATG TGA ACC

Reverse Primer:
5'-GTT TGC CAC TCA GAG AAT ACT GAA A

Probe:
6FAM-5'-CTG CGC CCG GAT CCA GGC-BHQ
```

Assay Tviri: This assay detects more than one species of mold: *Trichoderma viride, Trichoderma atroviride, Trichoderma koningii*

```
Forward Primer:
5'-CCC AAA CCC AAT GTG AAC CA

Reverse Primer:
5'-TCC GCG AGG GGA CTA CAG
```

```
Probe:
6FAM-CCC AAA CCC AAT GTG AAC CA-BHQ
```

*Wallemia sebi*

```
Forward Primer:
5'-GGC TTA GTG AAT CCT TCG GAG

Reverse Primer:
5'-GTT TAC CCA ACT TTG CAG TCC A

Probe:
6FAM-TGT GCC GTT GCC GGC TCA AAT AG-BHQ
```

Reference Spore Stock: *Geotrichum candidum* strain UAMH 7863

```
Forward Primer:
5'-GAT ATT TCT TGT GAA TTG CAG AAG TGA

Reverse Primer:
5'-TTG ATT CGA AAT TTT AGA AGA GCA AA

Probe:
6FAM-5'-CAA TTC CAA GAG AGA AAC AAC GCT CAA ACA
AG-BHQ
```

Recipe for making 37 assay master mixes for MSQPCR: Roche LightCycler 480 Probes Master cat#04707494001: 5 microliters per sample. For a 50 sample reaction kit will add 250 microliters to each assay. The 37 assay kit will use 9.25 milliliters of Roche LightCycler 480 Probes Master Mix divided up into 37 sterile eppendorf 1.5 milliliter snap cap tubes labeled with assay numbers 1 through 37. The Primers and Probes from above are mixed together into the working concentrations of 80 nM Probe and 1000 nM Primers. These prepared Primer/Probes are then used to mix with the Roche LightCycler 480 Probes blaster Mix: 1.4 microliters of the PrimerProbe mix per sample. For a 50 sample reaction kit add 70 microliters of each type of Primer/Probe mix to the corresponding labeled eppendorf tube.

The Master Mixes will be diluted with sterile PCR grade water (Provided with the Roche LightCycler 480 Probes Master Mix) to bring each master mix to the 7.5 microliter (5 microliters Master Mix, 1.4 microliters Primer/Probe and 1.1 microliters PCR Water) volume required per Sample, 1.1 microliters of water per sample. For a 50 sample reaction kit add 55 microliters to each assay tube for a total of 2,035 microliters of PCR grade water used per 50 sample reaction kit.

The Master Mixes are to be prepared using aseptic technique inside a biological safety hood to prevent contamination. Use the 20-200 microliter pipette for the Primers/Probes and water. Use the 100-1000 microliter pipette tor the Master Mix. Use the same aerosol filter DNA, Nuclease, and Endotoxin free pipette tips as before being sure to change tips after each assay and reagent.

Once the kit is prepared, one may store the kit for up to 2 months at a temperature of 4° C. (+/−1° C.). Run quality controls at the beginning of the kit, middle of the kit, and end of kit. Quality controls include a positive control to ensure the master mixes will indeed detect the spore species it is intended to detect. It also includes a negative control to ensure that the kit is not contaminated which may yield false positive results.

The following discusses how to process the calibration curves for MSQPCR analysis. For each assay, count the calibrator spore suspensions (made and counted in 0.5%

Tween 80) using a c-chip (microscope slide with a visible grid to use to count spores) and a microscope. Spore suspensions should reach a titer of $10^6$-$10^8$ spores/milliliter.

1. Add 10 microliters of each spore suspension to 200 microliters of AE Buffer (Qiagen) in separate bead tubes (same bead tubes used in extraction).
2. Bead-beat samples in the MagNA Lyser (6000 rpm, 14 sec) to form a crude lysate as before.
3. Using the spore titer calculated previously, perform serial dilutions (10 microliters lysate+90 microliters AE Buffer) of the crude lysate to a final dilution of $10^9$ (1-9 spores). Each species should be sufficiently replicated to provide standard deviations around each spore-dilution level. Crude extracts should be replicated to a total of three crude lysates.
4. Amplify each point in the Roche LightCycler using the same parameters as before. Each point in the dilution series should be a separate reaction on the PCR plate. Each point in each dilution series should be sufficiently replicated to ensure reliable CP occurrence. Each point in each dilution series should be replicated twice. Each dilution should have a total of six replicate CPs.
5. Once the LightCycler has finished, analyze the curves as before using the LightCycler software.
6. Perform partial linear regression analyses in Excel spreadsheets.
7. Use the "LOG" function to find the common log (base 10) of each reaction's initial spore concentration previously calculated with the c-chip. These values will constitute "KNOWN X's" required for downstream regression analyses.
8. Use the exported CPs from the Roche software to constitute "KNOWN Y's" required for downstream regression analyses.
9. Use the "SLOPE" function to generate each curve's slope (m).
10. Use the "INTERCEPT" function to generate each curve's y-intercept (b).

Absolute quantifications of each species can be performed using the equation:

$$y = m(\log x) + b \text{ where:}$$

y=CP of the unknown sample
x=concentration of the species' spores in the unknown sample
b=y-intercept of the species' calibration curve
m=slope of the species' calibration curve The equation can be manipulated for simple calculations using the derived equation:

$$\text{Spore concentration} = 10^{((CP-x)/m)}$$

This is the same equation used in the analysis of spores present on the capture medium.

The following are examples of calibration curve and standard curve values.

| Assay/Mold Species | Slope (m) | y-intercept (b) |
|---|---|---|
| Acremonium strictum | −3.6130 | 48.1783 |
| Alternaria alternata | −3.5970 | 39.7657 |
| Anigr | −3.2904 | 38.2156 |
| Aflav | −3.8277 | 42.9334 |
| Afumi | −2.6458 | 42.0075 |
| Aochr1 | −3.8558 | 51.0999 |
| Aspergillus penicillioides | −3.5529 | 23.1252 |
| Arest | −3.7382 | 42.3941 |
| Aspergillus sclerotiorum | −3.1404 | 39.2609 |

-continued

| Assay/Mold Species | Slope (m) | y-intercept (b) |
|---|---|---|
| Aspergillus sydowii | −3.0767 | 44.7056 |
| Aspergillus unguis | −3.1695 | 39.8130 |
| Aspergillus ustus | −3.2354 | 39.1928 |
| Aspergillus versicolor | −3.1844 | 41.2989 |
| Aureobasidium pullulans | −3.4945 | 41.4261 |
| Chaetomium globosum | −3.5615 | 38.8189 |
| Cladosporium cladosporioides svar. 1 | −3.5258 | 40.3226 |
| Cladosporium cladosporioides svar. 2 | −3.5677 | 37.8638 |
| Cladosporium herbarum | −3.8192 | 45.7793 |
| Eamst | −3.4000 | 39.4984 |
| Epicoccum nigrum | −3.4900 | 21.9884 |
| Muc1 | −3.6733 | 40.1932 |
| Paecilomyces variotii | −3.3491 | 39.4829 |
| PenGrp2 | −4.0742 | 52.6884 |
| Pbrev | −3.1073 | 40.1855 |
| Penicillium chrysogenum | −3.3305 | 43.8129 |
| Penicillium corylophilum | −2.9855 | 40.8585 |
| Penicillium purpurogenum | −3.3340 | 40.2322 |
| Penicillium variabile | −3.3912 | 39.7352 |
| Pspin2 | −3.6267 | 46.5456 |
| Rhizopus stolonifer | −3.6012 | 38.9658 |
| SCbrv | −3.5783 | 41.0178 |
| Scopulariopsis chartarum | −3.5027 | 35.5896 |
| Stachybotrys chartarum | −3.4337 | 40.8555 |
| Tviri | −3.3675 | 42.6956 |
| Wallemia sebi | −3.5677 | 41.3890 |
| Geotrichum candidum | −3.3548 | 37.4248 |

Interpreting reported results from MSQPCR air samples is very similar to the current method of result interpretation. The current norm is to compare the outside mold burden with the indoor mold harden. The biggest difference and main benefit of the MSQPCR method of detection is the ability of species identification of airborne molds. The current standard falls short to the MSQPCR analysis because it relies heavily on phenotypic characteristics such as color of spores, size of spores, and shapes of spores. These characteristics are used by a microscopist to identify the genus of the captured mold spores. Without culture techniques that could take up to two weeks to process, species identification from a microscopic exam sample is not possible. Another downfall of the current standard is the fact that many spores get grouped into a large category because there is not enough detail available on a standard spore trap to differentiate the spore any further. One example of this is the category Penicillium/Aspergillus-like. These spores are of the same color, shape, and size but their impact in a home are very different. Many Aspergillus species are pathogenic to humans and the ability to differentiate these species from other species of Penicillium/Aspergillus-like spores is very valuable. With the MSQPCR analysis the ability to rapidly, accurately, and with not only genus identification but species identification is achieved. MSQPCR does not have the human error associated with spore traps. MSQPCR uses DNA analysis which is 99.99% accurate. When a mold spore is detected and reported as Aspergillus fumigatus there is no doubt that is what is present.

Another benefit of the MSQPCR analysis is the ability to detect spores no matter how much particulate is present. Spore traps that are taken in areas where a high amount of particulate is present, such as a wall cavity, may not allow the microscopist to visually detect mold spores under the microscope. This is because the spore trap collects not only mold on the slide but drywall dust, which is difficult if not impossible to see through under a microscope. The capture medium disclosed herein will collect drywall dust, but does not rely on the human eye to detect mold spores. The mold spore DNA is purified before analysis which removes any contaminants such as drywall dust from the sample allowing the MSQPCR machine to detect the mold spores present without inhibition of particulate contamination. This yields a more accurate calculation of mold concentrations present.

Sampling Inside Versus Outside

There is currently no standard in the United States for the amount of acceptable concentrations of airborne mold found indoors. Current spore trap analysis, technically knows as direct microscopic exam, attempts to circumvent this issue by comparing indoor concentrations to outdoor concentrations. If the outdoor concentration is greater than the indoor, and no water intrusion or moisture evidence is present, the indoor environment is often considered to have a normal mold concentration or mold ecology by the investigator. In other words, the indoor concentration is congruent with the background, where the outside mold concentration serves as the background. Incongruence occurs when the indoor concentration is elevated compared to the background. Congruence is important, because the indoor versus outdoor comparison is often the leading evidence in court ligation and the proof required for insurance claims. While on the surface, outdoor versus indoor spore concentrations seem like a sensible method to evaluate an indoor environment for mold contamination; significant bias arise when the analytical method used to derive the comparison is direct microscopic exam. A major flaw exists in direct microscopic exam known as the group effect that has been virtually ignored by practitioners, the courts, and leading industry experts. The group effect is an artifact created by the inability of microscopic exam to distinguish between spores of similar morphology and size. The group effect is particularly problematic for the most common water intrusion molds, namely species in the genera *Penicillium* and *Aspergillus,* and is also prevalent with other species including the genus *Cladosporium.* In direct microscopic exam, all *Penicillium* and *Aspergillus* spores are grouped together and classified in the broad category *Penicillium/Aspergillus*-like. Spores of *Aspergillus fumigatus,* a water intrusion species that causes lung infection, are grouped with harmless mold species like *Aspergillus ustus* that are abundant outside. If the outside sample is greater than the inside sample, the practitioner will presume, falsely, that the indoor environment is not contaminated. In reality direct microscopic exam is in error because it provides the practitioner with a false negative result. Moreover, the group effect is not limited to *Penicillium* and *Aspergillus* species, the same holds true for *Cladosporium* spores and several other important indoor molds.

The ability of the MSQPCR analysis to classify mold spores into species rather than broad categorical groups is extremely valuable to prevent the biases associated with direct microscopic exam that lead to false negative and false positive results. MSQPCR eliminates the group effect and provides the practitioner with a reliable indoor versus outdoor mold concentration comparison. MSQPCR delivers the results required to determine if mold contamination is occurring indoors and if hazardous mold species are present.

Interpretation of Real Results

In the real life results below, the ability to compare the inside sample versus the outside sample is easy due to the proximity of the results. In this example, the results point to a hygiene issue because the same spore types are found indoors as outdoors and in lower concentrations indoors versus outdoors. If multiple mold species had been present in higher concentrations indoors as outdoors the hygienist would be able to suspect a water intrusion event and may suggest remediation based on his on-site findings.

| Species Identification | Spores/m³ Air Inside | Spores/m³ Air Outside |
|---|---|---|
| Acremonium strictum | Not Detected | Not Detected |
| Alternaria alternata | Not Detected | 6 |
| Anigr* | Not Detected | Not Detected |
| Aspergillus flavus/oryzae | Not Detected | Not Detected |
| Aspergillus fumigatus, Neosartorya fischeri | Not Detected | Not Detected |
| Aspergillus ochraceus/ostianus | Not Detected | Not Detected |
| Aspergillus penicillioides | Not Detected | Not Detected |
| Aspergillus restrictus/caesillus/conicus | Not Detected | Not Detected |
| Aspergillus sclerotiorum | Not Detected | Not Detected |
| Aspergillus sydowii | 1,728 | 2,130 |
| Aspergillus unguis | Not Detected | Not Detected |
| Aspergillus ustus | Not Detected | Not Detected |
| Aspergillus versicolor | Not Detected | Not Detected |
| Aureobasidium pullulans | Not Detected | Not Detected |
| Chaetomium globosum | Not Detected | Not Detected |
| Cladosporium cladosporioides svar. 1 | 145 | 15,033 |
| Cladosporium cladosporioides svar. 2 | Not Detected | 2 |
| Cladosporium herbarum | Not Detected | Not Detected |
| Cladosporium sphaerospermum | 95 | Not Detected |
| Earnst* | Not Detected | Not Detected |
| Epicoccum nigrum | Not Detected | 1 |
| Muc1* | Not Detected | Not Detected |
| Paecilomyces variotii | 27 | Not Detected |
| PenGrp2* | Not Detected | Not Detected |
| Penicillium brevicompactum/stoloniferum | Not Detected | Not Detected |
| Penicillum chrysogenum | Not Detected | Not Detected |
| Penicillium corylophilum | Not Detected | Not Detected |
| Penicillium purpurogenum | 61 | 67 |
| Penicillium variabile | Not Detected | Not Detected |
| Pspin2* | Not Detected | Not Detected |
| Rhizopus stolonifer | Not Detected | Not Detected |
| Scopulariopsis brevicaulis/fusca | Not Detected | Not Detected |
| Scopulariopsis chartarum | Not Detected | Not Detected |
| Stachybotrys chartarum | Not Detected | Not Detected |
| Trichoderma viride/atroviride/koningii | Not Detected | Not Detected |
| Wallemia sebi | Not Detected | Not Detected |
| Total Spores/m³ Air: | 2,055 | 17,239 |

The total spore count is also a good indication of moldiness of a home. Generally if the total spore counts indoors are higher than outdoors a mold problem may exist and should be investigated further. If they are lower a hygiene issue may be present or the home may have no issue at all.

Figure 13:
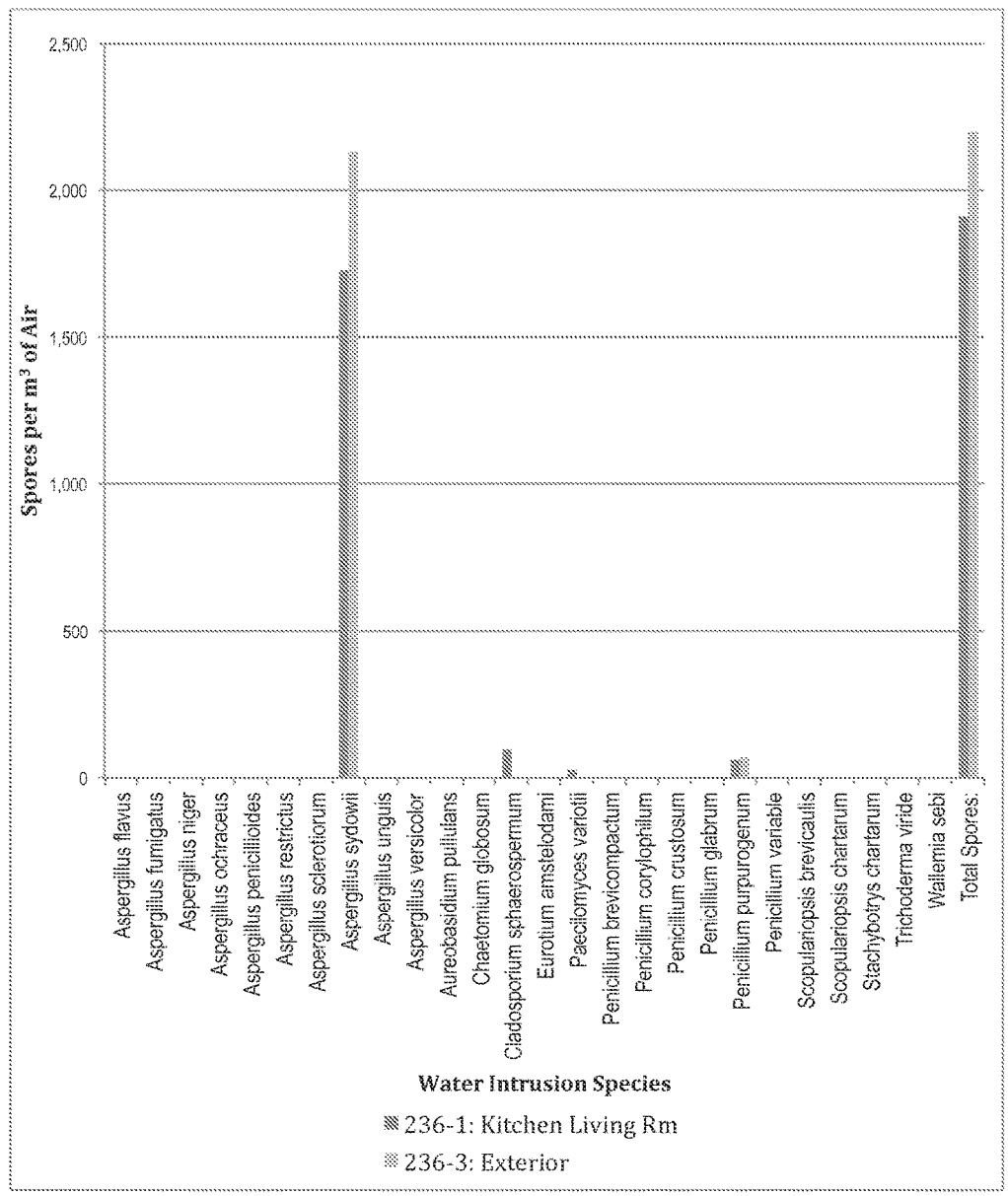
FIG. 13 is a bar graph depleting a comparison of water intrusion molds found in an actual indoor sample versus its outdoor sample.
Figure 14:
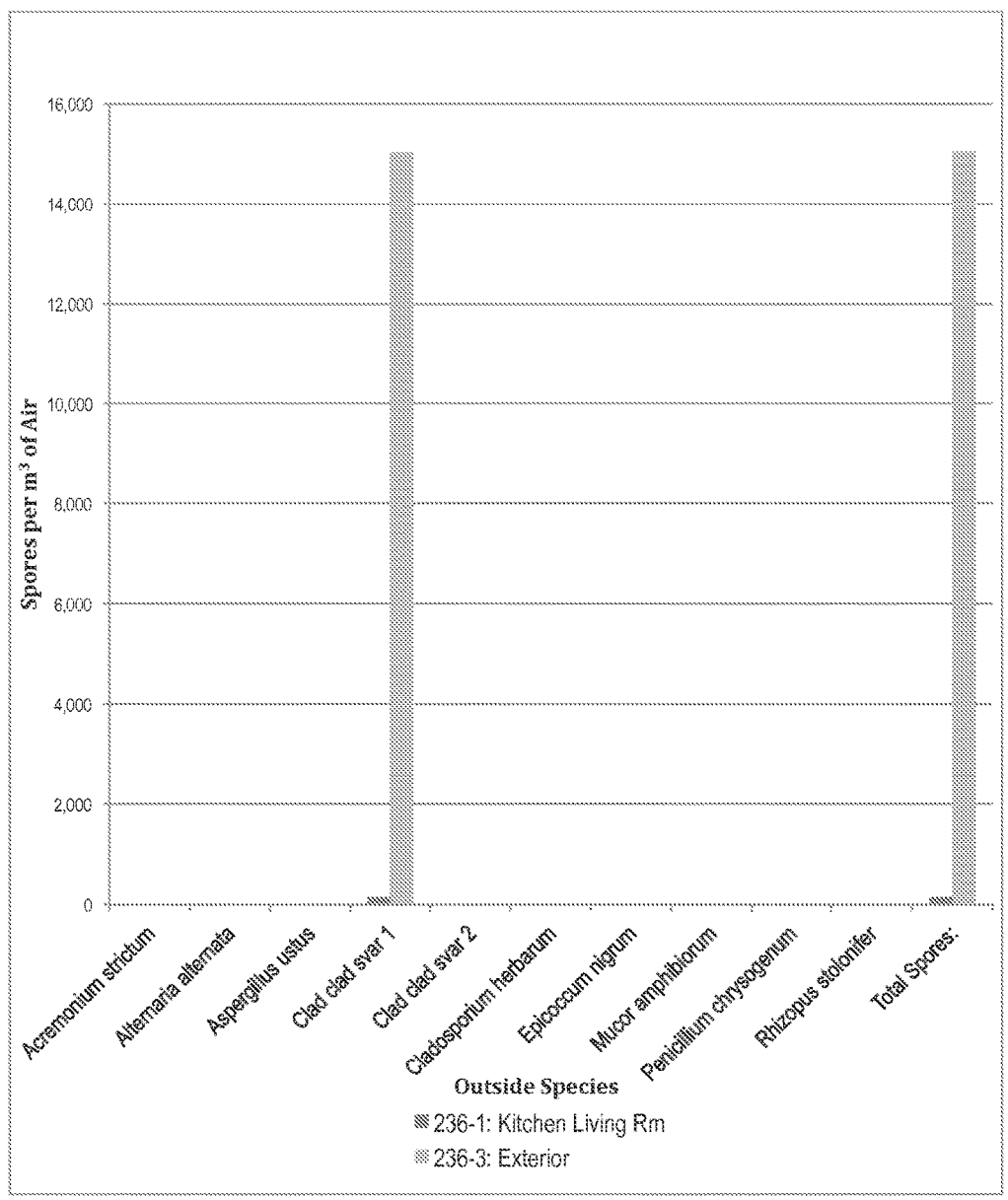
FIG. 14 is a bar graph depicting a comparison of outdoor molds found in an actual indoor sample versus its outdoor sample.

To aid in comparing the indoors versus the outdoors two bar graphs are shown in FIGS. 13 and 14 depicting comparing water intrusion molds and the other outdoor molds, respectively, detected in the real life results above.

It may be seen from these results that the mold present in this home is due to a hygiene issue and not an actively growing mold problem. All of the indoor molds present are either far less than their outdoor counterpart or are in low concentrations (<1,200 spores which is the spore count that may typically be used to cut off normal mold burden levels. Again, there is no standard on mold concentrations indoors. This value may be strictly used as a cutoff point.) It is ultimately up to the investigator to use this data and the on-site inspection to deduce a recommendation.

The Species identification of Airborne Molds is a collection of assays employing Mold Specific Quantitative Polymerase Chain Reaction (MSQPCR) technology. This technology was developed by the United States Environmental Protection Agency and is based upon more than a decade of research and development for indoor air fungi. MSQPCR, itself, is simply a method by which fungal DNA is copied. The action of copying the DNA coupled with a fluorescent probe makes it possible for fluorescent light to be detected. As more DNA is copied, more fluorescent light is produced. Perhaps most importantly, the entire process can be completed rapidly. The simplicity of this system translates into an analysis that is both robust and reliable. No other method currently used in indoor air quality can compare to the speed and reproducibility of MSQPCR.

This panel is designed to appeal to industrial hygienists and other highly trained and experienced individuals. As opposed to other panels offered for MSQPCR analysis, this panel carries with it no score that indicates relative moldiness. Instead, the Species ID panel emphasizes individual species quantifications and offers a granular assessment of the numbers of each fungal species or group of species detected. These raw numbers are emphasized over a score because they will be used by the hygienist to form recommendations and strategies for remediation.

To aid the hygienist receiving this report, a list of species descriptions has been complied and is provided with each report. Each description includes a brief statement relative to the natural and indoor ecology of the species, and observations of toxicity and/or pathogenicity are included when this information is known. Several commonalities can be noted for these species. Most, if not all, species of fungi occurring indoors are soilborne. Almost all of the species in this panel have worldwide distributions, rendering them useful indicators of indoor conditions in any location. Additionally, mycoses (fungal infections) have been documented for most of the species. Many mycoses occur in individuals with weakened or suppressed immune systems, and the presence of most species does not ensure infections to occur in occupants of homes. However, infections can and do occur in healthy people.

The following are examples of descriptions of the species.

*Alternaria alternata* is a fungus that can be found throughout the world on and in plants, soils, textiles and foods. *A. alternata* is among the most commonly observed molds in indoor environments, and its spores are released diurnally. It is found frequently in moist/humid areas such as water tanks and humidifiers. However, this species is also quite common in dry areas including dust from floors and mattresses. This species produces several allergens and mycotoxins (tenuazonic acid and altertoxins). Members of the genus *Alternaria* are known to cause asthma, sinusitis and infections of the eyes, ears and skin.

*Aspergillus flavus/oryzae:* Isolates of *Aspergillus flavus* and *A oryzae* are morphologically indistinguishable. *A. flavus* can be found virtually anywhere on Earth and has been isolated from dry areas in Chile, Antarctic lakes, humidifiers, plants, insects, animals, leather, feathers, cotton fabrics, paintings, etc. Distributions of *A. flavus* in American soils are denser in the southern U.S. *A. flavus* can produce aflatoxins under some circumstances. Aflatoxin B1 is the most potent carcinogen (cancer-causing agent) known, and lethal doses of this compound are known to be extremely low in mice. In man, *A. flavus* can cause pulmonary aspergillosis and weakened patients can suffer from cutaneous, nasal and cerebral infections.

*Aspergillus fumigatus/Neosartorya fischeri: Neosartorya fischeri* is a heat-tolerant fungus that is common in soil and fruits and occasionally causes human infections. *Aspergillus fumigatus* is also heat-tolerant and found worldwide. *A. fumigatus* is particularly dense in agricultural soils but is commonly isolated from house dust, garbage, compost, potted plants, humidifiers and HVAC systems, as well. More importantly, *A. fumigatus* is isolated commonly from human patients. In healthy humans, *A. fumigatus* is not a pathogen. However, this species can cause severe infections in humans with suppressed immune systems (e.g. those with pre-existing illnesses or taking immunosuppressants). In such individuals, spores that are inhaled are not attacked efficiently by the host's immune system, and the spores could germinate and begin to invade host tissues.

*Aspergillus niger/awamori/foetidus/phoenicis:* Species detected by this assay are morphologically similar and difficult to distinguish without molecular techniques, such as PCR. *Aspergillus awamori* is widespread in soils and on plants, and it has been used extensively for industrial applications and for food preparation. Some isolates of *A. awamori* have been found to produce the mycotoxin known as ochratoxin A, and it is possible that this fungus can cause subcutaneous infectious. *A. foetidus* and *A. phoenicis* are soil fungi that are likely involved in. natural decomposition. *A. niger* is a fungus that can be found in house dust and mattress dust. *A. niger* can also contaminate foods such as spices and onions. Importantly. *A. niger* is allergenic and can cause inner/outer ear infectious and sinus infections.

*Aspergillus ochraceus/ostianus:* These species of *Aspergillus* can be found indoors and on foodstuffs (e.g. coffee and paprika). Both species produce ochratoxin A, but *A. ostianus* can also produce aflatoxin.

*Aspergillus penicillioides:* This fungal species is common in very dry conditions and can be isolated from dried fruits, spices, archives, furniture, carpets, house dust and clothing. It is also associated with dust mites and is known to be allergenic.

*Aureobasidium pullulans:* This fungal species is ubiquitous, isolations are most common from plant leaves but have been successful from such diverse environments as humidifiers, house dust, mattress dust, forest soils, sand dunes, peat bogs, estuarine sediments, marine sediments and seawater. In British homes, airborne spores of this species increase sharply in winter months. Interestingly, *A. pullulans* does not appear to require high levels of nutrients commonly needed by other environmental microbes. This species is also extremely sensitive to heat, and can be found in high-humidity areas (e.g. window frames and bathrooms). This fungus is implicated rarely in human infections of the eyes and skin, and *A. pullulans* infections can be found in blood.

*Aspergillus restrictus/caesillus/conicus: Aspergillus restrictus* is a fungus that is more likely to be isolated in cool and dry climates, which could explain its frequent occurrence in house dust. All three of these species are considered medically important, although infections are not widely documented.

*Aspergillus sclerotiorum:* This species is found in tropical and subtropical soils across the world *A. sclerotiorum* can produce ochratoxins and is known to cause infections of the ear, toenails and fingernails.

*Acremonium strictum:* This species is a common inhabitant of soils worldwide and can be isolated from plant surfaces, fuel and fuel filters. Import in an indoor context, *A. strictum* is found widely in the atmosphere and is commonly observed on food and moist indoor surfaces (e.g. humidifiers). It is possible that moldy homes can show greater numbers of this species in winter months. *A. strictum* has caused infections in chemotherapy and transplant patients. Infections of blood, cerebrospinal fluid, eyes, pulmonary, peritoneal, toenails and fingernails have been reported for this species, although they appear to be relatively rare. However, reports of infections by species of the genus Acremonium appear to be on the rise.

*Aspergillus sydowii:* This species is found in soils worldwide and has been isolated from plants, seeds, foods, leather, textiles and uranium mines. *A. sydowii* can produce mycotoxins know as sydowic acids and can cause fingernail and toenail infections and invasive aspergillosis.

*Aspergillus unguis:* Very little is known about this fungal species. However, it has been found to cause fingernail and toenail infections.

*Aspergillus ustus:* It is likely that *A. ustus* is one of the most widely spread species of *Aspergillus*. It has been isolated from diverse soils from around the world, salt marshes, estuaries, foods, bat caves and uranium mines. Sporulation of *A. ustus* is stimulated by light. This species produces several mycotoxins and has been responsible for endocarditis and infections of the lungs and skin. It is possible that infection by *A. ustus* is nosocomial, but diagnoses of this mycosis are rare.

*Aspergillus versicolor:* As are most *aspergilli, A. versicolor* is extremely widespread in nature. However, this species tends to occupy the coldest regions of *Aspergillus* distributions, as well as deserts, peat bogs, estuarine sediments, compost, linoleum, chipboard, paintings, cheeses, spices, stored grains, house dust, mattress dust and rotting military equipment in the tropics. This species is extremely xerophilic and common in indoor environments, where its growth can cause moldy odors. *A. versicolor* is known to produce a carcinogenic compound known as sterigmatocystin. *A. versicolor* is allergenic, and mycoses of this species include osteomyelitis and infections of the auditory canal, fingernails and toenails.

*Cladosporium cladosporioides* svar. 1 and *Cladosporium cladosporioides* svar. 2: These two organisms are not currently recognized as individual species, and they cannot be differentiated using standard microscopic techniques. DNA sequencing projects seeking to devise rapid identification methods for fungal pathogens detected distinct DNA sequences in this species, and each is now recognized as a "sequevar." In essence, they cannot be identified correctly without the use of DNA-based technology, such as this quantitative PCR technique. Both sequevars represent the most common saprobe in the environment. This species generates many more spores under moist conditions than in dry conditions. *C. cladosporioides* is distributed worldwide in soils, the air, house dust, mattress dust, on dairy products, textiles, food, plants, many aquatic environments, wood pulp and feathers. This species is allergenic and can form fungal balls in lungs, skin infections, keratitis, sinusitis, and infections of spinal fluid, fingernails and toenails.

*Chaetomium globosum:* This fungus is isolated commonly from soil, decaying plants, seeds, food, estuarine environments and marine sediments. It has particular notoriety as a soft rot fungus and can be found on decaying wood, explaining its occurrence in indoor environments following water damage. In fact, *C. globosum* can be found growing on wallpaper in homes with extensive water damage. Sporulation of this fungus tends to occur more readily under dark conditions, and the spores produced are very resistant to desiccation. While not particularly allergenic itself, its presence appears to enhance the allergic response of individuals to other allergens (e.g. pollen). This species has caused invasive lung infections, subcutaneous infections and fingernail and toenail infections. The genes *Chaetomium* appears to be emerging as important fungal pathogens.

*Cladosporium herbarum:* This is a very common fungus in nature, and it can be isolated from dead/dying plants, soil, food, wheat, textiles, floor dust, mattress dust seawater, uranium mines and paint. In fact, it is possible that *C. herbarum* is the most common *Cladosporium* in air samples and appears to be more prevalent in summer months in British homes. However, this species was found to cause food spoilage at refrigeration temperatures. *C. herbarum* was found to be strongly allergenic and produces an endotoxin that has similar health effects to that produced by *Stachybotrys chartarum*.

*Cladosporium sphaerospermum:* As with most species of *Cladosporium, C. sphaerospermum* is common worldwide. This species can be isolated from plants, soil, food, paint, textiles, insulation, floor dust, mattress dust, humidifiers and from humans and other animals. Spores of this species are difficult to distinguish from those of *C. cladosporioides* microscopically, but DNA analyses easily distinguish them. *C. sphaerospermum* is one of the most commonly isolated indoor air fungi. This species is allergenic and has caused documented bronchial lesions and subcutaneous skin infections.

*Eurotium (Aspergillus) amstelodami/chevalieri/herbariorum/rubrum/repens:* This assay identifies a group of closely related *Eurotium* species. Most molds isolated from indoor environments are sexual species, however some also reproduce sexually. To discern these two modes of reproductive states, mycologists have devised a unique terminology. The term "anamorph" describes those molds that reproduce asexually; whereas, the term, "teleomorph" describes molds that reproduce sexually. Anamorphic or asexual molds do not need a partner to reproduce, they produce their spores similar to budding yeast cells and do so on a grand scale; millions if not billions of spores are produced in a short period of time (24-48 hrs). Anamorphic reproduction is an evolutionary strategy that fires the conflict between humans and molds in homes and buildings; just add water to building materials, and mold will seem to appear out of nowhere and rapidly colonize the damp substrates. Teleomorphic molds, however, must find and fuse with a compatible partner or strain in order to produce spores sexually. Hence, teleomorphic molds are rare relative to anamorphic molds because the paring of compatible strains in the environment is governed by the laws of probability, and the probability of two microscopic strains meeting at any given location is remote. However, some teleomorphic species tend to commonly occur indoors.

The most common teleomorphic genus is *Eurotium. Eurotium* species are perhaps the most abundant sexually reproducing molds found indoors. The key to *Eurotium's* success lies in genetics, for *Eurotium's* asexual counterpart is *Aspergillus. Aspergillus* species produce enormous flushes of spores. Hence, *Aspergillus* spores are extremely common, especially in a water compromised building. The relative abundance of *Aspergillus* spores dramatically increases the probability that two compatible *aspergilli* strains will meet and fuse to form a teleomorphic *eurotium* species. Thus, *Eurotium* has become an important mold genus, one that should not be ignored during indoor air quality assessments. This genus is xerophilic and has the ability to germinate and colonize substrates having minimal water activity. *Eurotium* is also a common food spoilage organism.

*Eurotium* has been implicated in several health maladies. Anamorphic forms of *Eurotium* produce various mycotoxins. Farmer's lung disease (FLD) is caused mainly by repeated exposure to moldy hay colonized by *Eurotium* species. *Eurotium* may produce a respiratory allergic reaction in susceptible individuals and can cause adverse health effects in children who attend school in buildings damaged by moisture.

*Epicoccum nigrum:* One of the most commonly isolated indoor fungi, *E. nigrum* is also widely distributed in nature. It can be found growing in and on soils, sand, dead/decaying plant tissue, saline environments, textiles and moldy paper. At this time, *E. nigrum* is not known as a pathogen, but this species can cause skin allergies.

*Mucor amphibiorum/circinelloides/hiemalis/indicus/mucedo/racemosus/ramosissimus* and *Rhizopus azygosporus/homothalicus/microsporus/oligosporus/oryzae:* The species of mold represented in this assay are all members of a broad class of fungi known as zygomycetes. Zygomycetes are primitive but fast growing fungi. They are widely distributed in terrestrial environments, where they break down plant debris in soil. However, many species are common environmental contaminants that can cause food spoilage, and a few are pathogens of plants, insects and humans. By definition, all pathogenic zygomycotic species will grow at 37° C., with the possible exception of the *M. circinelloides*.

The common genera that infect humans include *Rhizopus*, followed by *Mucor, Rhizomucor, Absidia, Cunninghamella* and *Syncephalastrum*. Underlying diseases in humans include cancer and leukemia, antibiotic or prednisone use, diabetes, deferoxamine, and desferrioxamine therapy, transplantation, burn wounds and the associated forms of immunosuppressive therapies. The most common clinical form of zygomycosis is rhinocerebral disease followed by pulmonary, cutaneous/subcutaueous, gastrointestinal and disseminated disease. *Mucor amphibiorum* has not been reported in human infections. *Mucor circinelloides* has been reported as a rare cause of cutaneous infections in humans. *Mucor hiemalis* has been reported from a few cases of human cutaneous infection. *Mucor indicus* (synonym: *M. rouxii*) has been reported from human gastric and pulmonary infections, a case of necrotizing fasciitis and reports of hepatic infection in a bone marrow transplant recipient who had ingested contaminated medicine. *Mucor racemosus* has been infrequently reported as a causative agent of animal and human zygomycosis. *Rhizopus microsporus* accounts for 10-15% of reported human cases and has been implicated in cellulitis, cutaneous infection, zygomycosis, and gastrointestinal infections. However, rhinocerebral forms of *R. microsporus* are rare. *Rhizopus oryzae* (synonym: *R. arrhizus*) is the most common causative agent of zygomycosis, accounting for 60% of the reported culture positive cases and nearly 90 percent of the rhinocerebral form of infection.

*Penicillium brevicompactum/stoloniferum: P. stoloniferum* is a relatively rarely occurring fungus found in soils and foods. *P. stoloniferum* commonly attacks poinsettias in Switzerland greenhouses but is not currently recognized as a health threat. *P. brevicompactum* is a common species worldwide and indoors, occurring in fruit juices, fresh herbs, wall paper, wood, paint, potted plants (particularly strong association), soils, floor dust, mattress dust, caves, freshwater and uranium mines. *P. brevicompactum* can be xerophilic sensitive to high-salt conditions. This species also inhibits the growth of several species of soil bacteria, possibly through production of its several mycotoxins (e.g. ochratoxin). *P. brevicompactum* can be strongly allergenic, but it has not been implicated widely in human disease. However, *P. brevicompactum* has been isolated from a dog with fungal pneumonia and a deep organ infection in a human.

*Penicillium chrysogenum:* This species is found world wide but has earned most notoriety from its production of penicillin. In addition to soil distributions, it can be isolated from foods, plants, floor dust, mattress dust, wood, wall paper, paint, gypsum (as in wall board) artwork and occasionally optical lenses. It is considered a good indicator of water intrusion. Although this species is highly allergenic and can produce mycotoxins, *P. chrysogenum* is not considered a common health risk. Nonetheless, infections of the ears, eyes, heart tissue, skin and cerebrospinal fluid have been documented.

*Penicillium corylophilum:* This species is widely distributed, but it is found more frequently in warm climates. Isolations have been successful from soil, textiles and various foods. This species is thought to be relatively xerophilic and is likely more common in low-humidity conditions, probably explaining their isolation from wood and paint. At this time, *P. corylophilum* does not appear to be a human pathogen.

*Penicillium crustosum/camemberti/commune/echinulatum/solitum: P. crustosum* is a common food contaminant, particularly common in seeds, nuts and apples. *P. crustosum* produces potent neurotoxins (penitrems and roquefortine) that can cause muscular tremors in individuals eating contaminated foods. *P. camemberti* is a mold commonly found in cheeses (camembert cheese) and occasionally meats, where it can produce low levels of the mycotoxin cyclopiazonic acid. *P. commune* is commonly found indoors and on cheeses and meats. *P. commune* has been documented in pulmonary infections in dogs and can produce cyclopiazonic acid and possibly nephrotoxins. *P. echinulatum* found most frequently on foods containing oils (e.g. margarine and cheese) but is also found indoors. *P. echinulatum* is capable of producing tremorgenic mycotoxins (territrems). *P. solitum* is commonly isolated from foods such as hard cheeses and some meats. *P. solitum* can produce mycotoxins (viridicatins) on such foods but does not appear to cause diseases in humans.

*Penicillium purpurogenum:* This is another example of a *Penicillium* with a worldwide distribution in soils. This species also occurs on foods, plants and occasionally on optical lenses. *P. purpurogenum* tends to grow in environments with low pH (acidic). A mycotoxin, known as rubratoxin, can be produced when growth occurs on foods, *P. purpurogenum* is not currently recognized as a pathogen, but it has caused a few pulmonary infections in humans and a systemic infection in a dog.

*Penicillium glabrum/lividum/purpurescens/spinulosum/thomii: P. glabrum* is a commonly occurring indoor fungus, but it can also be found contaminating foods (particularly fruit and fruit products) and growing in compost and aggressively on computer diskettes in high humidity. *P. glabrum* also grows well on the corks of wine bottles and elicits allergic responses in individuals that work with wine corks. *P. lividum* is a relatively rare and non-pathogenic species of *Penicillium* and occurs mostly in northern latitudes. *P. purpurescens* is a common inhabitant of soils and indoor environments (particularly greenhouses). *P. purpurescens* does not appear to be an overt pathogen, but it can be found in feed potentially toxic to poultry. *P. spinulosum* is distributed worldwide and is usually found associated with forest soils, flour-based foods and fruit products. *P. spinulosum* can grow on wet plasterboard, and such growth can yield mycotoxin production, the health effects of which are under debate. *P. thomii* is widely distributed in soils of temperate environments. *P. thomii* does not appear to be pathogenic, given current data.

*Penicillium variabile:* This species is widely distributed in soils and can also be found in seawater, fruit juices, paper and optical lenses. *P. variabile* appears to grow best at slightly acidic pH and does not tolerate high heat for long periods of time. This species produces ochratoxin A (among others) but is not currently known as a pathogen.

*Paecilomyces variotii:* This fungus is known to be heat resistant and can, therefore, be found most commonly in warm and arid environments. It is also very common in air, animal feed, seawater, wood pulp in paper mills, creosote-treated wood, walls, wallpaper, house dust, compost, leather, optical lenses, synthetic rubber, photographic paper, moldy cigars, ink, PVC and kerosene. *P. variotii* has been known as a pathogen in birds and mammals but also appears to be an important human pathogen and infects the heart, lungs, bones, spleen and soft tissue.

*Rhizopus stolonifer:* This fungus has a worldwide distribution, occurring most densely in soils of warm climates. *R. stolonifer* is one of the most frequently observed indoor air fungi and commonly grows on foods (e.g. bread) and its spores can germinate on moist paper. It appears that growth is enhanced by slightly alkaline conditions. This species has caused occasional infectious, but it is not generally regarded as an important pathogen.

*Scopulariopsis brevicaulis/fusca: S. brevicaulis* is the most common species of its genus and occurs worldwide in soils, floor dust, mattress dust, aquatic environments, compost, seawater, paper mill waste, wood pulp, textiles, paintings and uranium mines. *S. fusca* is also commonly isolated from soil, straw, paper and food. *S. brevicaulis* is regarded as moderately xerophilic, and it can produce toxic by-products of arsenic and memory, becoming exceptionally dangerous when growing indoors on paints containing arsenic. *S. brevicaulis* is said to produce garlic- or ammonia-like odors when growing indoors. *S. brevicaulis* attacks hairs and keratin, often leading to infections of the toenails and fingernails. However, it can also cause skin, lung and soft tissue infections. *S. fusca* is less frequently pathogenic than *S. brevicaulis*, this species produces infections of the skin, fingernails and toenails.

*Scopulariopsis chartarum:* Relatively little is known about *Scopulariopsis chartarum*, not to be confused with *Stachybotrys chartarum*. *Scopulariopsis chartarum* was first observed on wallpaper, but has also been found in soils. Growth on maple by this species results in a weakening of the wood. This species does not appear to be a human pathogen, but it has caused a systemic mycosis in a dog.

*Stachybotrys chartarum: Stachybotrys chartarum* is the quintessential black mold found in indoor environments. It is distributed worldwide, primarily found associated on decaying plant material. *S chartarum* possesses a battery of enzymes linked to plant decomposition, making it a potent attacker of all forms of wood, paper and natural fibers (e.g. wool). Hence, it is commonly an indicator of moisture problems in homes and can be found growing on paper, wallpaper, wall board, wood and textiles. *S. chartarum* is not a common pathogen, in and of itself, but has garnered particular attention for its role in Sick Building Syndrome, due to its high production of mycotoxins (satratoxin G and H). Long-term exposure to such toxins can induce a myriad of health maladies, including nausea, dermatitis, rhinitis, depression, general malaise, headaches, sore throats, etc. *S. chartarum* has also been known to invade lung tissue.

*Trichoderma viride/atroviride/koningii: T. viride* and *T. koningii* are cosmopolitan species and have been isolated from almost every environment. Soils, composts and vegetables are common sources of these fungi, and cool and moist environments are preferred. Very little is known about *T. atroviride. T. viride* can grow on linoleum and wallpaper, and is probably more commonly isolated from indoor environments in winter months. As a genus, *Irichoderma* can cause nosocomial (hospital acquired) mycoses from contaminated solutions. *T. viride* is allergenic and has caused keratitis, peritonitis, pulmonary infections and hematomas.

*Wallemia sebi:* This fungus is a very common indoor fungus and is commonly found airborne. It is xerophilic and osmophilic and can be found growing on substrates that would desiccate many other fungi. These substrates include rock salt, bacon, salted foods, jam, jellies, fruits, textiles, rotting paper, and mammals. *W. sebi* can also be found in floor dust, mattress dust, soil and hay. This species is allergenic and is known to colonize human lungs, bones and skin. However, *W. sebi* is not considered a serious pathogen.

Although the particular embodiments shown and described above will prove to be useful in many applications in air sampling of biological compounds art to which the present invention pertains, further modifications of the present invention will occur to persons skilled in the art. All such modifications are deemed to be within the scope and spirit of the present invention as defined by the appended claims.

What is claimed is:

1. An air sampling matrix comprising:
   an air sampling capture matrix substrate comprising a plurality of woven fibers having a biomixture coating applied over the substrate fibers, wherein the biomixture comprises
   a. a mixture of a water soluble synthetic polymer with water; and
   b. from about 0.005 to about 0.1 parts per billion (ppb) of a glycoprotein added to the polymer-water mixture for forming a liquid biomixture; and
   a plurality of microbial propagules collected on the biomixture coated fibers.

2. The composition of claim 1, wherein the water soluble polymer comprises polyvinyl alcohol.

3. The composition of claim 1, wherein the glycoprotein comprises fibronectin.

4. The composition of claim 1, wherein the woven fibers comprises polyester spun fibers.

5. The composition of claim 4, wherein the polyester spun fibers comprise polyethylene terephthalate.

6. A method of collecting microbial propagules, comprising:
   a. applying a liquid biomixture to an air sampling capture matrix substrate comprising a plurality of woven fibers, wherein the biomixture comprises a mixture of a water soluble synthetic polymer, water, and from about 0.005 to about 0.1 parts per billion (ppb) of a glycoprotein;
   b. making a fluid connection between the substrate and a vacuum pump for collecting an air sample therethrough; and
   collecting a plurality of the microbial propagules on the biomixture coated fibers.

7. The method of claim 6, wherein the water soluble polymer comprises polyvinyl alcohol.

8. The method of claim 6, wherein the glycoprotein comprises fibronectin.

9. The method of claim 6, wherein the woven fibers comprises polyester spun fibers.

10. The method of claim 9, wherein the polyester spun fibers further comprise polyethylene terephthalate.

* * * * *

SEQUENCE LISTING

```
<160> NUMBER OF SEQ ID NOS: 216

<210> SEQ ID NO 1
<211> LENGTH: 24
<212> TYPE: DNA
<213> ORGANISM: Artificial sequence
<220> FEATURE:
<223> OTHER INFORMATION: Synthesized Primer

<400> SEQUENCE: 1
caacccattg tgaacttacc aaac                                        24

<210> SEQ ID NO 2
<211> LENGTH: 22
<212> TYPE: DNA
<213> ORGANISM: Artificial sequence
<220> FEATURE:
<223> OTHER INFORMATION: Synthesized Primer
```

```
<400> SEQUENCE: 2
cgcccctcag agaaatacga tt                                         22

<210> SEQ ID NO 3
<211> LENGTH: 18
<212> TYPE: DNA
<213> ORGANISM: Artificial sequence
<220> FEATURE:
<223> OTHER INFORMATION: Synthesized Probe

<400> SEQUENCE: 3
tcagcgcgcg gtggcctc                                              18

<210> SEQ ID NO 4
<211> LENGTH: 16
<212> TYPE: DNA
<213> ORGANISM: Artificial sequence
<220> FEATURE:
<223> OTHER INFORMATION: Synthesized Primer

<400> SEQUENCE: 4
ggcgggctgg aacctc                                                16

<210> SEQ ID NO 5
<211> LENGTH: 29
<212> TYPE: DNA
<213> ORGANISM: Artificial sequence
<220> FEATURE:
<223> OTHER INFORMATION: Synthesized Primer

<400> SEQUENCE: 5
gcaattacaa aaggtttatg tttgtcgta                                  29

<210> SEQ ID NO 6
<211> LENGTH: 34
<212> TYPE: DNA
<213> ORGANISM: Artificial sequence
<220> FEATURE:
<223> OTHER INFORMATION: Synthesized Probe

<400> SEQUENCE: 6
ttacagcctt gctgaattat tcacccttgt cttt                            34

<210> SEQ ID NO 7
<211> LENGTH: 17
<212> TYPE: DNA
<213> ORGANISM: Artificial sequence
<220> FEATURE:
<223> OTHER INFORMATION: Synthesized Primer

<400> SEQUENCE: 7
gccggagacc ccaacac                                               17

<210> SEQ ID NO 8
<211> LENGTH: 26
<212> TYPE: DNA
<213> ORGANISM: Artificial sequence
<220> FEATURE:
<223> OTHER INFORMATION: Synthesized Primer

<400> SEQUENCE: 8
tgttgaaagt tttaactgat tgcatt                                     26

<210> SEQ ID NO 9
<211> LENGTH: 30
```

```
<212> TYPE: DNA
<213> ORGANISM: Artificial sequence
<220> FEATURE:
<223> OTHER INFORMATION: Synthesized Probe

<400> SEQUENCE: 9
aatcaactca gactgcacgc tttcagacag                                      30

<210> SEQ ID NO 10
<211> LENGTH: 17
<212> TYPE: DNA
<213> ORGANISM: Artificial sequence
<220> FEATURE:
<223> OTHER INFORMATION: Synthesized Primer

<400> SEQUENCE: 10
gccggagacc ccaacac                                                    17

<210> SEQ ID NO 11
<211> LENGTH: 26
<212> TYPE: DNA
<213> ORGANISM: Artificial sequence
<220> FEATURE:
<223> OTHER INFORMATION: Synthesized Primer

<400> SEQUENCE: 11
tgttgaaagt tttaactgat tgcatt                                          26

<210> SEQ ID NO 12
<211> LENGTH: 30
<212> TYPE: DNA
<213> ORGANISM: Artificial sequence
<220> FEATURE:
<223> OTHER INFORMATION: Synthesized Probe

<400> SEQUENCE: 12
aatcaactca gactgcacgc tttcagacag                                      30

<210> SEQ ID NO 13
<211> LENGTH: 17
<212> TYPE: DNA
<213> ORGANISM: Artificial sequence
<220> FEATURE:
<223> OTHER INFORMATION: Synthesized Primer

<400> SEQUENCE: 13
gccggagacc ccaacac                                                    17

<210> SEQ ID NO 14
<211> LENGTH: 26
<212> TYPE: DNA
<213> ORGANISM: Artificial sequence
<220> FEATURE:
<223> OTHER INFORMATION: Synthesized Primer

<400> SEQUENCE: 14
tgttgaaagt tttaactgat tgcatt                                          26

<210> SEQ ID NO 15
<211> LENGTH: 30
<212> TYPE: DNA
<213> ORGANISM: Artificial sequence
<220> FEATURE:
<223> OTHER INFORMATION: Synthesized Probe

<400> SEQUENCE: 15
```

```
aatcaactca gactgcacgc tttcagacag                                    30

<210> SEQ ID NO 16
<211> LENGTH: 17
<212> TYPE: DNA
<213> ORGANISM: Artificial sequence
<220> FEATURE:
<223> OTHER INFORMATION: Synthesized Primer

<400> SEQUENCE: 16
gccggagacc ccaacac                                                  17

<210> SEQ ID NO 17
<211> LENGTH: 26
<212> TYPE: DNA
<213> ORGANISM: Artificial sequence
<220> FEATURE:
<223> OTHER INFORMATION: Synthesized Primer

<400> SEQUENCE: 17
tgttgaaagt tttaactgat tgcatt                                        26

<210> SEQ ID NO 18
<211> LENGTH: 30
<212> TYPE: DNA
<213> ORGANISM: Artificial sequence
<220> FEATURE:
<223> OTHER INFORMATION: Synthesized Probe

<400> SEQUENCE: 18
aatcaactca gactgcacgc tttcagacag                                    30

<210> SEQ ID NO 19
<211> LENGTH: 21
<212> TYPE: DNA
<213> ORGANISM: Artificial sequence
<220> FEATURE:
<223> OTHER INFORMATION: Synthesized Primer

<400> SEQUENCE: 19
cgagtgtagg gttcctagcg a                                             21

<210> SEQ ID NO 20
<211> LENGTH: 15
<212> TYPE: DNA
<213> ORGANISM: Artificial sequence
<220> FEATURE:
<223> OTHER INFORMATION: Synthesized Primer

<400> SEQUENCE: 20
ccggcggcca tgaat                                                    15

<210> SEQ ID NO 21
<211> LENGTH: 31
<212> TYPE: DNA
<213> ORGANISM: Artificial sequence
<220> FEATURE:
<223> OTHER INFORMATION: Synthesized Probe

<400> SEQUENCE: 21
tcccacccgt gtttactgta ccttagttgc t                                  31

<210> SEQ ID NO 22
<211> LENGTH: 21
<212> TYPE: DNA
<213> ORGANISM: Artificial sequence
```

```
<220> FEATURE:
<223> OTHER INFORMATION: Synthesized Primer

<400> SEQUENCE: 22
cgagtgtagg gttcctagcg a                                          21

<210> SEQ ID NO 23
<211> LENGTH: 15
<212> TYPE: DNA
<213> ORGANISM: Artificial sequence
<220> FEATURE:
<223> OTHER INFORMATION: Synthesized Primer

<400> SEQUENCE: 23
ccggcggcca tgaat                                                 15

<210> SEQ ID NO 24
<211> LENGTH: 31
<212> TYPE: DNA
<213> ORGANISM: Artificial sequence
<220> FEATURE:
<223> OTHER INFORMATION: Synthesized Probe

<400> SEQUENCE: 24
tcccacccgt gtttactgta ccttagttgc t                                31

<210> SEQ ID NO 25
<211> LENGTH: 15
<212> TYPE: DNA
<213> ORGANISM: Artificial sequence
<220> FEATURE:
<223> OTHER INFORMATION: Synthesized Primer

<400> SEQUENCE: 25
gcccgccgtt tcgac                                                 15

<210> SEQ ID NO 26
<211> LENGTH: 27
<212> TYPE: DNA
<213> ORGANISM: Artificial sequence
<220> FEATURE:
<223> OTHER INFORMATION: Synthesized Primer

<400> SEQUENCE: 26
ccgttgttga aagttttaac tgattac                                     27

<210> SEQ ID NO 27
<211> LENGTH: 21
<212> TYPE: DNA
<213> ORGANISM: Artificial sequence
<220> FEATURE:
<223> OTHER INFORMATION: Synthesized Probe

<400> SEQUENCE: 27
cccgccgaag accccaacat g                                          21

<210> SEQ ID NO 28
<211> LENGTH: 15
<212> TYPE: DNA
<213> ORGANISM: Artificial sequence
<220> FEATURE:
<223> OTHER INFORMATION: Synthesized Primer

<400> SEQUENCE: 28
gcccgccgtt tcgac                                                 15
```

<210> SEQ ID NO 29
<211> LENGTH: 27
<212> TYPE: DNA
<213> ORGANISM: Artificial sequence
<220> FEATURE:
<223> OTHER INFORMATION: Synthesized Primer

<400> SEQUENCE: 29
ccgttgttga agtttttaac tgattac                                27

<210> SEQ ID NO 30
<211> LENGTH: 21
<212> TYPE: DNA
<213> ORGANISM: Artificial sequence
<220> FEATURE:
<223> OTHER INFORMATION: Synthesized Probe

<400> SEQUENCE: 30
cccgccgaag accccaacat g                                      21

<210> SEQ ID NO 31
<211> LENGTH: 21
<212> TYPE: DNA
<213> ORGANISM: Artificial sequence
<220> FEATURE:
<223> OTHER INFORMATION: Synthesized Primer

<400> SEQUENCE: 31
aacctcccac ccgtgtatac c                                      21

<210> SEQ ID NO 32
<211> LENGTH: 15
<212> TYPE: DNA
<213> ORGANISM: Artificial sequence
<220> FEATURE:
<223> OTHER INFORMATION: Synthesized Primer

<400> SEQUENCE: 32
ccggcgagcg ctgtg                                             15

<210> SEQ ID NO 33
<211> LENGTH: 22
<212> TYPE: DNA
<213> ORGANISM: Artificial sequence
<220> FEATURE:
<223> OTHER INFORMATION: Synthesized Probe

<400> SEQUENCE: 33
accttgttgc ttcggcgagc cc                                     22

<210> SEQ ID NO 34
<211> LENGTH: 21
<212> TYPE: DNA
<213> ORGANISM: Artificial sequence
<220> FEATURE:
<223> OTHER INFORMATION: Synthesized Primer

<400> SEQUENCE: 34
aacctcccac ccgtgtatac c                                      21

<210> SEQ ID NO 35
<211> LENGTH: 15
<212> TYPE: DNA
<213> ORGANISM: Artificial sequence
<220> FEATURE:
<223> OTHER INFORMATION: Synthesized Primer

<400> SEQUENCE: 35
ccggcgagcg ctgtg                                                          15

<210> SEQ ID NO 36
<211> LENGTH: 22
<212> TYPE: DNA
<213> ORGANISM: Artificial sequence
<220> FEATURE:
<223> OTHER INFORMATION: Synthesized Probe

<400> SEQUENCE: 36
accttgttgc ttcggcgagc cc                                                  22

<210> SEQ ID NO 37
<211> LENGTH: 17
<212> TYPE: DNA
<213> ORGANISM: Artificial sequence
<220> FEATURE:
<223> OTHER INFORMATION: Synthesized Primer

<400> SEQUENCE: 37
cgccggagac ctcaacc                                                        17

<210> SEQ ID NO 38
<211> LENGTH: 23
<212> TYPE: DNA
<213> ORGANISM: Artificial sequence
<220> FEATURE:
<223> OTHER INFORMATION: Synthesized Primer

<400> SEQUENCE: 38
tccgttgttg aaagttttaa cga                                                 23

<210> SEQ ID NO 39
<211> LENGTH: 33
<212> TYPE: DNA
<213> ORGANISM: Artificial sequence
<220> FEATURE:
<223> OTHER INFORMATION: Synthesized Probe

<400> SEQUENCE: 39
tgaacactgt ctgaaggttg cagtctgagt atg                                      33

<210> SEQ ID NO 40
<211> LENGTH: 14
<212> TYPE: DNA
<213> ORGANISM: Artificial sequence
<220> FEATURE:
<223> OTHER INFORMATION: Synthesized Primer

<400> SEQUENCE: 40
gggcccgcct tcat                                                           14

<210> SEQ ID NO 41
<211> LENGTH: 27
<212> TYPE: DNA
<213> ORGANISM: Artificial sequence
<220> FEATURE:
<223> OTHER INFORMATION: Synthesized Primer

<400> SEQUENCE: 41
gttgttgaaa gttttaacga tttttct                                             27

<210> SEQ ID NO 42

-continued

<210> SEQ ID NO 42
<211> LENGTH: 22
<212> TYPE: DNA
<213> ORGANISM: Artificial sequence
<220> FEATURE:
<223> OTHER INFORMATION: Synthesized Probe

<400> SEQUENCE: 42
cccgccggag actccaacat tg                                          22

<210> SEQ ID NO 43
<211> LENGTH: 14
<212> TYPE: DNA
<213> ORGANISM: Artificial sequence
<220> FEATURE:
<223> OTHER INFORMATION: Synthesized Primer

<400> SEQUENCE: 43
gggcccgcct tcat                                                   14

<210> SEQ ID NO 44
<211> LENGTH: 27
<212> TYPE: DNA
<213> ORGANISM: Artificial sequence
<220> FEATURE:
<223> OTHER INFORMATION: Synthesized Primer

<400> SEQUENCE: 44
gttgttgaaa gttttaacga tttttct                                     27

<210> SEQ ID NO 45
<211> LENGTH: 22
<212> TYPE: DNA
<213> ORGANISM: Artificial sequence
<220> FEATURE:
<223> OTHER INFORMATION: Synthesized Probe

<400> SEQUENCE: 45
cccgccggag actccaacat tg                                          22

<210> SEQ ID NO 46
<211> LENGTH: 14
<212> TYPE: DNA
<213> ORGANISM: Artificial sequence
<220> FEATURE:
<223> OTHER INFORMATION: Synthesized Primer

<400> SEQUENCE: 46
gggcccgcct tcat                                                   14

<210> SEQ ID NO 47
<211> LENGTH: 27
<212> TYPE: DNA
<213> ORGANISM: Artificial sequence
<220> FEATURE:
<223> OTHER INFORMATION: Synthesized Primer

<400> SEQUENCE: 47
gttgttgaaa gttttaacga tttttct                                     27

<210> SEQ ID NO 48
<211> LENGTH: 22
<212> TYPE: DNA
<213> ORGANISM: Artificial sequence
<220> FEATURE:
<223> OTHER INFORMATION: Synthesized Probe

<400> SEQUENCE: 48
cccgccggag actccaacat tg                                              22

<210> SEQ ID NO 49
<211> LENGTH: 22
<212> TYPE: DNA
<213> ORGANISM: Artificial sequence
<220> FEATURE:
<223> OTHER INFORMATION: Synthesized Primer

<400> SEQUENCE: 49
attactgagt gagggtccct cg                                              22

<210> SEQ ID NO 50
<211> LENGTH: 19
<212> TYPE: DNA
<213> ORGANISM: Artificial sequence
<220> FEATURE:
<223> OTHER INFORMATION: Synthesized Primer

<400> SEQUENCE: 50
cctagggagg ggggtttga                                                  19

<210> SEQ ID NO 51
<211> LENGTH: 22
<212> TYPE: DNA
<213> ORGANISM: Artificial sequence
<220> FEATURE:
<223> OTHER INFORMATION: Synthesized Probe

<400> SEQUENCE: 51
cccgccgaag caacaaggta cg                                              22

<210> SEQ ID NO 52
<211> LENGTH: 18
<212> TYPE: DNA
<213> ORGANISM: Artificial sequence
<220> FEATURE:
<223> OTHER INFORMATION: Synthesized Primer

<400> SEQUENCE: 52
caacctccca cccgagaa                                                   18

<210> SEQ ID NO 53
<211> LENGTH: 28
<212> TYPE: DNA
<213> ORGANISM: Artificial sequence
<220> FEATURE:
<223> OTHER INFORMATION: Synthesized Primer

<400> SEQUENCE: 53
ccattgttga aagttttgac tgatctta                                        28

<210> SEQ ID NO 54
<211> LENGTH: 31
<212> TYPE: DNA
<213> ORGANISM: Artificial sequence
<220> FEATURE:
<223> OTHER INFORMATION: Synthesized Probe

<400> SEQUENCE: 54
agactgcatc actctcaggc atgaagttca g                                    31

<210> SEQ ID NO 55
<211> LENGTH: 22
<212> TYPE: DNA

```
<213> ORGANISM: Artificial sequence
<220> FEATURE:
<223> OTHER INFORMATION: Synthesized Primer

<400> SEQUENCE: 55
caacctccca cccttgaata ct                                          22

<210> SEQ ID NO 56
<211> LENGTH: 23
<212> TYPE: DNA
<213> ORGANISM: Artificial sequence
<220> FEATURE:
<223> OTHER INFORMATION: Synthesized Primer

<400> SEQUENCE: 56
tcactctcag gcatgaagtt cag                                         23

<210> SEQ ID NO 57
<211> LENGTH: 23
<212> TYPE: DNA
<213> ORGANISM: Artificial sequence
<220> FEATURE:
<223> OTHER INFORMATION: Synthesized Probe

<400> SEQUENCE: 57
cactgttgct tcggcgagga gcc                                         23

<210> SEQ ID NO 58
<211> LENGTH: 23
<212> TYPE: DNA
<213> ORGANISM: Artificial sequence
<220> FEATURE:
<223> OTHER INFORMATION: Synthesized Primer

<400> SEQUENCE: 58
aaggatcatt accgagtgca tgt                                         23

<210> SEQ ID NO 59
<211> LENGTH: 18
<212> TYPE: DNA
<213> ORGANISM: Artificial sequence
<220> FEATURE:
<223> OTHER INFORMATION: Synthesized Primer

<400> SEQUENCE: 59
gccgaagcaa cgttggtc                                               18

<210> SEQ ID NO 60
<211> LENGTH: 19
<212> TYPE: DNA
<213> ORGANISM: Artificial sequence
<220> FEATURE:
<223> OTHER INFORMATION: Synthesized Probe

<400> SEQUENCE: 60
cccccgggca ggcctaacc                                              19

<210> SEQ ID NO 61
<211> LENGTH: 14
<212> TYPE: DNA
<213> ORGANISM: Artificial sequence
<220> FEATURE:
<223> OTHER INFORMATION: Synthesized Primer

<400> SEQUENCE: 61
cggcggggag ccct                                                   14
```

<210> SEQ ID NO 62
<211> LENGTH: 28
<212> TYPE: DNA
<213> ORGANISM: Artificial sequence
<220> FEATURE:
<223> OTHER INFORMATION: Synthesized Primer

<400> SEQUENCE: 62
ccattgttga agttttgac tgatctta                                    28

<210> SEQ ID NO 63
<211> LENGTH: 31
<212> TYPE: DNA
<213> ORGANISM: Artificial sequence
<220> FEATURE:
<223> OTHER INFORMATION: Synthesized Probe

<400> SEQUENCE: 63
agactgcatc actctcaggc atgaagttca g                               31

<210> SEQ ID NO 64
<211> LENGTH: 25
<212> TYPE: DNA
<213> ORGANISM: Artificial sequence
<220> FEATURE:
<223> OTHER INFORMATION: Synthesized Primer

<400> SEQUENCE: 64
gatcattaaa gagtaagggt gctca                                      25

<210> SEQ ID NO 65
<211> LENGTH: 18
<212> TYPE: DNA
<213> ORGANISM: Artificial sequence
<220> FEATURE:
<223> OTHER INFORMATION: Synthesized Primer

<400> SEQUENCE: 65
gctcgcctgg gacgaatc                                              18

<210> SEQ ID NO 66
<211> LENGTH: 21
<212> TYPE: DNA
<213> ORGANISM: Artificial sequence
<220> FEATURE:
<223> OTHER INFORMATION: Synthesized Probe

<400> SEQUENCE: 66
cgcccgacct ccaacccttt g                                          21

<210> SEQ ID NO 67
<211> LENGTH: 17
<212> TYPE: DNA
<213> ORGANISM: Artificial sequence
<220> FEATURE:
<223> OTHER INFORMATION: Synthesized Primer

<400> SEQUENCE: 67
ccgcaggccc tgaaaag                                               17

<210> SEQ ID NO 68
<211> LENGTH: 13
<212> TYPE: DNA
<213> ORGANISM: Artificial sequence
<220> FEATURE:

<223> OTHER INFORMATION: Synthesized Primer

<400> SEQUENCE: 68
cgcggcgcga cca                                                          13

<210> SEQ ID NO 69
<211> LENGTH: 30
<212> TYPE: DNA
<213> ORGANISM: Artificial sequence
<220> FEATURE:
<223> OTHER INFORMATION: Synthesized Probe

<400> SEQUENCE: 69
agatgtatgc tactacgctc ggtgcgacag                                        30

<210> SEQ ID NO 70
<211> LENGTH: 24
<212> TYPE: DNA
<213> ORGANISM: Artificial sequence
<220> FEATURE:
<223> OTHER INFORMATION: Synthesized Primer

<400> SEQUENCE: 70
cattacaagt gaccccggtc taac                                              24

<210> SEQ ID NO 71
<211> LENGTH: 17
<212> TYPE: DNA
<213> ORGANISM: Artificial sequence
<220> FEATURE:
<223> OTHER INFORMATION: Synthesized Primer

<400> SEQUENCE: 71
ccccggaggc aacagag                                                      17

<210> SEQ ID NO 72
<211> LENGTH: 28
<212> TYPE: DNA
<213> ORGANISM: Artificial sequence
<220> FEATURE:
<223> OTHER INFORMATION: Synthesized Probe

<400> SEQUENCE: 72
ccgggatgtt cataaccctt tgttgtcc                                          28

<210> SEQ ID NO 73
<211> LENGTH: 20
<212> TYPE: DNA
<213> ORGANISM: Artificial sequence
<220> FEATURE:
<223> OTHER INFORMATION: Synthesized Primer

<400> SEQUENCE: 73
tacaagtgac cccggctacg                                                   20

<210> SEQ ID NO 74
<211> LENGTH: 17
<212> TYPE: DNA
<213> ORGANISM: Artificial sequence
<220> FEATURE:
<223> OTHER INFORMATION: Synthesized Primer

<400> SEQUENCE: 74
ccccggaggc aacagag                                                      17

<210> SEQ ID NO 75
<211> LENGTH: 28
<212> TYPE: DNA
<213> ORGANISM: Artificial sequence
<220> FEATURE:
<223> OTHER INFORMATION: Synthesized Probe

<400> SEQUENCE: 75
ccgggatgtt cataaccctt tgttgtcc                                28

<210> SEQ ID NO 76
<211> LENGTH: 16
<212> TYPE: DNA
<213> ORGANISM: Artificial sequence
<220> FEATURE:
<223> OTHER INFORMATION: Synthesized Primer

<400> SEQUENCE: 76
aagaacgccc gggctt                                             16

<210> SEQ ID NO 77
<211> LENGTH: 22
<212> TYPE: DNA
<213> ORGANISM: Artificial sequence
<220> FEATURE:
<223> OTHER INFORMATION: Synthesized Primer

<400> SEQUENCE: 77
cgcaagagtt tgaagtgtcc ac                                      22

<210> SEQ ID NO 78
<211> LENGTH: 34
<212> TYPE: DNA
<213> ORGANISM: Artificial sequence
<220> FEATURE:
<223> OTHER INFORMATION: Synthesized Probe

<400> SEQUENCE: 78
ctggttattc ataacccttt gttgtccgac tctg                         34

<210> SEQ ID NO 79
<211> LENGTH: 17
<212> TYPE: DNA
<213> ORGANISM: Artificial sequence
<220> FEATURE:
<223> OTHER INFORMATION: Synthesized Primer

<400> SEQUENCE: 79
accggctggg tctttcg                                            17

<210> SEQ ID NO 80
<211> LENGTH: 19
<212> TYPE: DNA
<213> ORGANISM: Artificial sequence
<220> FEATURE:
<223> OTHER INFORMATION: Synthesized Primer

<400> SEQUENCE: 80
ggggttgttt tacggcgtg                                          19

<210> SEQ ID NO 81
<211> LENGTH: 20
<212> TYPE: DNA
<213> ORGANISM: Artificial sequence
<220> FEATURE:
<223> OTHER INFORMATION: Synthesized Probe

<400> SEQUENCE: 81
cccgcggcac cctttagcga                                            20

<210> SEQ ID NO 82
<211> LENGTH: 17
<212> TYPE: DNA
<213> ORGANISM: Artificial sequence
<220> FEATURE:
<223> OTHER INFORMATION: Synthesized Primer

<400> SEQUENCE: 82
gtggcggcac catgtct                                               17

<210> SEQ ID NO 83
<211> LENGTH: 23
<212> TYPE: DNA
<213> ORGANISM: Artificial sequence
<220> FEATURE:
<223> OTHER INFORMATION: Synthesized Primer

<400> SEQUENCE: 83
ctggttaaaa agattggttg cga                                        23

<210> SEQ ID NO 84
<211> LENGTH: 22
<212> TYPE: DNA
<213> ORGANISM: Artificial sequence
<220> FEATURE:
<223> OTHER INFORMATION: Synthesized Probe

<400> SEQUENCE: 84
cagctggacc tacgggagcg gg                                         22

<210> SEQ ID NO 85
<211> LENGTH: 17
<212> TYPE: DNA
<213> ORGANISM: Artificial sequence
<220> FEATURE:
<223> OTHER INFORMATION: Synthesized Primer

<400> SEQUENCE: 85
gtggcggcac catgtct                                               17

<210> SEQ ID NO 86
<211> LENGTH: 23
<212> TYPE: DNA
<213> ORGANISM: Artificial sequence
<220> FEATURE:
<223> OTHER INFORMATION: Synthesized Primer

<400> SEQUENCE: 86
ctggttaaaa agattggttg cga                                        23

<210> SEQ ID NO 87
<211> LENGTH: 22
<212> TYPE: DNA
<213> ORGANISM: Artificial sequence
<220> FEATURE:
<223> OTHER INFORMATION: Synthesized Probe

<400> SEQUENCE: 87
cagctggacc tacgggagcg gg                                         22

<210> SEQ ID NO 88
<211> LENGTH: 17

```
<212> TYPE: DNA
<213> ORGANISM: Artificial sequence
<220> FEATURE:
<223> OTHER INFORMATION: Synthesized Primer

<400> SEQUENCE: 88
gtggcggcac catgtct                                                    17

<210> SEQ ID NO 89
<211> LENGTH: 23
<212> TYPE: DNA
<213> ORGANISM: Artificial sequence
<220> FEATURE:
<223> OTHER INFORMATION: Synthesized Primer

<400> SEQUENCE: 89
ctggttaaaa agattggttg cga                                             23

<210> SEQ ID NO 90
<211> LENGTH: 22
<212> TYPE: DNA
<213> ORGANISM: Artificial sequence
<220> FEATURE:
<223> OTHER INFORMATION: Synthesized Probe

<400> SEQUENCE: 90
cagctggacc tacgggagcg gg                                              22

<210> SEQ ID NO 91
<211> LENGTH: 17
<212> TYPE: DNA
<213> ORGANISM: Artificial sequence
<220> FEATURE:
<223> OTHER INFORMATION: Synthesized Primer

<400> SEQUENCE: 91
gtggcggcac catgtct                                                    17

<210> SEQ ID NO 92
<211> LENGTH: 23
<212> TYPE: DNA
<213> ORGANISM: Artificial sequence
<220> FEATURE:
<223> OTHER INFORMATION: Synthesized Primer

<400> SEQUENCE: 92
ctggttaaaa agattggttg cga                                             23

<210> SEQ ID NO 93
<211> LENGTH: 22
<212> TYPE: DNA
<213> ORGANISM: Artificial sequence
<220> FEATURE:
<223> OTHER INFORMATION: Synthesized Probe

<400> SEQUENCE: 93
cagctggacc tacgggagcg gg                                              22

<210> SEQ ID NO 94
<211> LENGTH: 17
<212> TYPE: DNA
<213> ORGANISM: Artificial sequence
<220> FEATURE:
<223> OTHER INFORMATION: Synthesized Primer

<400> SEQUENCE: 94
```

-continued

| | |
|---|---|
| gtggcggcac catgtct | 17 |

<210> SEQ ID NO 95
<211> LENGTH: 23
<212> TYPE: DNA
<213> ORGANISM: Artificial sequence
<220> FEATURE:
<223> OTHER INFORMATION: Synthesized Primer

<400> SEQUENCE: 95

| | |
|---|---|
| ctggttaaaa agattggttg cga | 23 |

<210> SEQ ID NO 96
<211> LENGTH: 22
<212> TYPE: DNA
<213> ORGANISM: Artificial sequence
<220> FEATURE:
<223> OTHER INFORMATION: Synthesized Probe

<400> SEQUENCE: 96

| | |
|---|---|
| cagctggacc tacgggagcg gg | 22 |

<210> SEQ ID NO 97
<211> LENGTH: 26
<212> TYPE: DNA
<213> ORGANISM: Artificial sequence
<220> FEATURE:
<223> OTHER INFORMATION: Synthesized Primer

<400> SEQUENCE: 97

| | |
|---|---|
| ttgtagactt cggtctgcta cctctt | 26 |

<210> SEQ ID NO 98
<211> LENGTH: 22
<212> TYPE: DNA
<213> ORGANISM: Artificial sequence
<220> FEATURE:
<223> OTHER INFORMATION: Synthesized Primer

<400> SEQUENCE: 98

| | |
|---|---|
| tgcaactgca aagggtttga at | 22 |

<210> SEQ ID NO 99
<211> LENGTH: 31
<212> TYPE: DNA
<213> ORGANISM: Artificial sequence
<220> FEATURE:
<223> OTHER INFORMATION: Synthesized Probe

<400> SEQUENCE: 99

| | |
|---|---|
| catgtctttt gagtaccttc gtttcctcgg c | 31 |

<210> SEQ ID NO 100
<211> LENGTH: 16
<212> TYPE: DNA
<213> ORGANISM: Artificial sequence
<220> FEATURE:
<223> OTHER INFORMATION: Synthesized Primer

<400> SEQUENCE: 100

| | |
|---|---|
| caccgcccgt cgctac | 16 |

<210> SEQ ID NO 101
<211> LENGTH: 25
<212> TYPE: DNA
<213> ORGANISM: Artificial sequence

```
<220> FEATURE:
<223> OTHER INFORMATION: Synthesized Primer

<400> SEQUENCE: 101
cctagtttgc catagttctc agcag                                              25

<210> SEQ ID NO 102
<211> LENGTH: 33
<212> TYPE: DNA
<213> ORGANISM: Artificial sequence
<220> FEATURE:
<223> OTHER INFORMATION: Synthesized Probe

<400> SEQUENCE: 102
ccgattgaat ggttatagtg agcatatggg atc                                     33

<210> SEQ ID NO 103
<211> LENGTH: 16
<212> TYPE: DNA
<213> ORGANISM: Artificial sequence
<220> FEATURE:
<223> OTHER INFORMATION: Synthesized Primer

<400> SEQUENCE: 103
caccgcccgt cgctac                                                        16

<210> SEQ ID NO 104
<211> LENGTH: 25
<212> TYPE: DNA
<213> ORGANISM: Artificial sequence
<220> FEATURE:
<223> OTHER INFORMATION: Synthesized Primer

<400> SEQUENCE: 104
cctagtttgc catagttctc agcag                                              25

<210> SEQ ID NO 105
<211> LENGTH: 33
<212> TYPE: DNA
<213> ORGANISM: Artificial sequence
<220> FEATURE:
<223> OTHER INFORMATION: Synthesized Probe

<400> SEQUENCE: 105
ccgattgaat ggttatagtg agcatatggg atc                                     33

<210> SEQ ID NO 106
<211> LENGTH: 16
<212> TYPE: DNA
<213> ORGANISM: Artificial sequence
<220> FEATURE:
<223> OTHER INFORMATION: Synthesized Primer

<400> SEQUENCE: 106
caccgcccgt cgctac                                                        16

<210> SEQ ID NO 107
<211> LENGTH: 25
<212> TYPE: DNA
<213> ORGANISM: Artificial sequence
<220> FEATURE:
<223> OTHER INFORMATION: Synthesized Primer

<400> SEQUENCE: 107
cctagtttgc catagttctc agcag                                              25
```

```
<210> SEQ ID NO 108
<211> LENGTH: 33
<212> TYPE: DNA
<213> ORGANISM: Artificial sequence
<220> FEATURE:
<223> OTHER INFORMATION: Synthesized Probe

<400> SEQUENCE: 108
ccgattgaat ggttatagtg agcatatggg atc                             33

<210> SEQ ID NO 109
<211> LENGTH: 16
<212> TYPE: DNA
<213> ORGANISM: Artificial sequence
<220> FEATURE:
<223> OTHER INFORMATION: Synthesized Primer

<400> SEQUENCE: 109
caccgcccgt cgctac                                                16

<210> SEQ ID NO 110
<211> LENGTH: 25
<212> TYPE: DNA
<213> ORGANISM: Artificial sequence
<220> FEATURE:
<223> OTHER INFORMATION: Synthesized Primer

<400> SEQUENCE: 110
cctagtttgc catagttctc agcag                                      25

<210> SEQ ID NO 111
<211> LENGTH: 33
<212> TYPE: DNA
<213> ORGANISM: Artificial sequence
<220> FEATURE:
<223> OTHER INFORMATION: Synthesized Probe

<400> SEQUENCE: 111
ccgattgaat ggttatagtg agcatatggg atc                             33

<210> SEQ ID NO 112
<211> LENGTH: 16
<212> TYPE: DNA
<213> ORGANISM: Artificial sequence
<220> FEATURE:
<223> OTHER INFORMATION: Synthesized Primer

<400> SEQUENCE: 112
caccgcccgt cgctac                                                16

<210> SEQ ID NO 113
<211> LENGTH: 25
<212> TYPE: DNA
<213> ORGANISM: Artificial sequence
<220> FEATURE:
<223> OTHER INFORMATION: Synthesized Primer

<400> SEQUENCE: 113
cctagtttgc catagttctc agcag                                      25

<210> SEQ ID NO 114
<211> LENGTH: 33
<212> TYPE: DNA
<213> ORGANISM: Artificial sequence
<220> FEATURE:
<223> OTHER INFORMATION: Synthesized Probe
```

<400> SEQUENCE: 114
ccgattgaat ggttatagtg agcatatggg atc        33

<210> SEQ ID NO 115
<211> LENGTH: 16
<212> TYPE: DNA
<213> ORGANISM: Artificial sequence
<220> FEATURE:
<223> OTHER INFORMATION: Synthesized Primer

<400> SEQUENCE: 115
caccgcccgt cgctac        16

<210> SEQ ID NO 116
<211> LENGTH: 25
<212> TYPE: DNA
<213> ORGANISM: Artificial sequence
<220> FEATURE:
<223> OTHER INFORMATION: Synthesized Primer

<400> SEQUENCE: 116
cctagtttgc catagttctc agcag        25

<210> SEQ ID NO 117
<211> LENGTH: 33
<212> TYPE: DNA
<213> ORGANISM: Artificial sequence
<220> FEATURE:
<223> OTHER INFORMATION: Synthesized Probe

<400> SEQUENCE: 117
ccgattgaat ggttatagtg agcatatggg atc        33

<210> SEQ ID NO 118
<211> LENGTH: 16
<212> TYPE: DNA
<213> ORGANISM: Artificial sequence
<220> FEATURE:
<223> OTHER INFORMATION: Synthesized Primer

<400> SEQUENCE: 118
caccgcccgt cgctac        16

<210> SEQ ID NO 119
<211> LENGTH: 25
<212> TYPE: DNA
<213> ORGANISM: Artificial sequence
<220> FEATURE:
<223> OTHER INFORMATION: Synthesized Primer

<400> SEQUENCE: 119
cctagtttgc catagttctc agcag        25

<210> SEQ ID NO 120
<211> LENGTH: 33
<212> TYPE: DNA
<213> ORGANISM: Artificial sequence
<220> FEATURE:
<223> OTHER INFORMATION: Synthesized Probe

<400> SEQUENCE: 120
ccgattgaat ggttatagtg agcatatggg atc        33

<210> SEQ ID NO 121

```
<211> LENGTH: 16
<212> TYPE: DNA
<213> ORGANISM: Artificial sequence
<220> FEATURE:
<223> OTHER INFORMATION: Synthesized Primer

<400> SEQUENCE: 121
caccgcccgt cgctac                                                    16

<210> SEQ ID NO 122
<211> LENGTH: 25
<212> TYPE: DNA
<213> ORGANISM: Artificial sequence
<220> FEATURE:
<223> OTHER INFORMATION: Synthesized Primer

<400> SEQUENCE: 122
cctagtttgc catagttctc agcag                                          25

<210> SEQ ID NO 123
<211> LENGTH: 33
<212> TYPE: DNA
<213> ORGANISM: Artificial sequence
<220> FEATURE:
<223> OTHER INFORMATION: Synthesized Probe

<400> SEQUENCE: 123
ccgattgaat ggttatagtg agcatatggg atc                                 33

<210> SEQ ID NO 124
<211> LENGTH: 16
<212> TYPE: DNA
<213> ORGANISM: Artificial sequence
<220> FEATURE:
<223> OTHER INFORMATION: Synthesized Primer

<400> SEQUENCE: 124
caccgcccgt cgctac                                                    16

<210> SEQ ID NO 125
<211> LENGTH: 25
<212> TYPE: DNA
<213> ORGANISM: Artificial sequence
<220> FEATURE:
<223> OTHER INFORMATION: Synthesized Primer

<400> SEQUENCE: 125
cctagtttgc catagttctc agcag                                          25

<210> SEQ ID NO 126
<211> LENGTH: 33
<212> TYPE: DNA
<213> ORGANISM: Artificial sequence
<220> FEATURE:
<223> OTHER INFORMATION: Synthesized Probe

<400> SEQUENCE: 126
ccgattgaat ggttatagtg agcatatggg atc                                 33

<210> SEQ ID NO 127
<211> LENGTH: 16
<212> TYPE: DNA
<213> ORGANISM: Artificial sequence
<220> FEATURE:
<223> OTHER INFORMATION: Synthesized Primer

<400> SEQUENCE: 127
```

```
caccgcccgt cgctac                                              16

<210> SEQ ID NO 128
<211> LENGTH: 25
<212> TYPE: DNA
<213> ORGANISM: Artificial sequence
<220> FEATURE:
<223> OTHER INFORMATION: Synthesized Primer

<400> SEQUENCE: 128
cctagtttgc catagttctc agcag                                    25

<210> SEQ ID NO 129
<211> LENGTH: 33
<212> TYPE: DNA
<213> ORGANISM: Artificial sequence
<220> FEATURE:
<223> OTHER INFORMATION: Synthesized Probe

<400> SEQUENCE: 129
ccgattgaat ggttatagtg agcatatggg atc                           33

<210> SEQ ID NO 130
<211> LENGTH: 16
<212> TYPE: DNA
<213> ORGANISM: Artificial sequence
<220> FEATURE:
<223> OTHER INFORMATION: Synthesized Primer

<400> SEQUENCE: 130
caccgcccgt cgctac                                              16

<210> SEQ ID NO 131
<211> LENGTH: 25
<212> TYPE: DNA
<213> ORGANISM: Artificial sequence
<220> FEATURE:
<223> OTHER INFORMATION: Synthesized Primer

<400> SEQUENCE: 131
cctagtttgc catagttctc agcag                                    25

<210> SEQ ID NO 132
<211> LENGTH: 33
<212> TYPE: DNA
<213> ORGANISM: Artificial sequence
<220> FEATURE:
<223> OTHER INFORMATION: Synthesized Probe

<400> SEQUENCE: 132
ccgattgaat ggttatagtg agcatatggg atc                           33

<210> SEQ ID NO 133
<211> LENGTH: 16
<212> TYPE: DNA
<213> ORGANISM: Artificial sequence
<220> FEATURE:
<223> OTHER INFORMATION: Synthesized Primer

<400> SEQUENCE: 133
caccgcccgt cgctac                                              16

<210> SEQ ID NO 134
<211> LENGTH: 25
<212> TYPE: DNA
```

```
<213> ORGANISM: Artificial sequence
<220> FEATURE:
<223> OTHER INFORMATION: Synthesized Primer

<400> SEQUENCE: 134
cctagtttgc catagttctc agcag                                           25

<210> SEQ ID NO 135
<211> LENGTH: 33
<212> TYPE: DNA
<213> ORGANISM: Artificial sequence
<220> FEATURE:
<223> OTHER INFORMATION: Synthesized Probe

<400> SEQUENCE: 135
ccgattgaat ggttatagtg agcatatggg atc                                  33

<210> SEQ ID NO 136
<211> LENGTH: 17
<212> TYPE: DNA
<213> ORGANISM: Artificial sequence
<220> FEATURE:
<223> OTHER INFORMATION: Synthesized Primer

<400> SEQUENCE: 136
cgaagacccc tggaacg                                                    17

<210> SEQ ID NO 137
<211> LENGTH: 29
<212> TYPE: DNA
<213> ORGANISM: Artificial sequence
<220> FEATURE:
<223> OTHER INFORMATION: Synthesized Primer

<400> SEQUENCE: 137
gttgttgaaa gttttaattg attgattgt                                       29

<210> SEQ ID NO 138
<211> LENGTH: 23
<212> TYPE: DNA
<213> ORGANISM: Artificial sequence
<220> FEATURE:
<223> OTHER INFORMATION: Synthesized Probe

<400> SEQUENCE: 138
ctcagacggc aaccttccag gca                                             23

<210> SEQ ID NO 139
<211> LENGTH: 15
<212> TYPE: DNA
<213> ORGANISM: Artificial sequence
<220> FEATURE:
<223> OTHER INFORMATION: Synthesized Primer

<400> SEQUENCE: 139
cgggcccgcc ttaac                                                      15

<210> SEQ ID NO 140
<211> LENGTH: 36
<212> TYPE: DNA
<213> ORGANISM: Artificial sequence
<220> FEATURE:
<223> OTHER INFORMATION: Synthesized Primer

<400> SEQUENCE: 140
gaaagtttta aataatttat attttcactc agagtt                               36
```

<210> SEQ ID NO 141
<211> LENGTH: 17
<212> TYPE: DNA
<213> ORGANISM: Artificial sequence
<220> FEATURE:
<223> OTHER INFORMATION: Synthesized Probe

<400> SEQUENCE: 141
cgcgcccgcc gaagaca                                                17

<210> SEQ ID NO 142
<211> LENGTH: 15
<212> TYPE: DNA
<213> ORGANISM: Artificial sequence
<220> FEATURE:
<223> OTHER INFORMATION: Synthesized Primer

<400> SEQUENCE: 142
cgggcccgcc ttaac                                                  15

<210> SEQ ID NO 143
<211> LENGTH: 36
<212> TYPE: DNA
<213> ORGANISM: Artificial sequence
<220> FEATURE:
<223> OTHER INFORMATION: Synthesized Primer

<400> SEQUENCE: 143
gaaagtttta aataatttat attttcactc agagtt                           36

<210> SEQ ID NO 144
<211> LENGTH: 17
<212> TYPE: DNA
<213> ORGANISM: Artificial sequence
<220> FEATURE:
<223> OTHER INFORMATION: Synthesized Probe

<400> SEQUENCE: 144
cgcgcccgcc gaagaca                                                17

<210> SEQ ID NO 145
<211> LENGTH: 15
<212> TYPE: DNA
<213> ORGANISM: Artificial sequence
<220> FEATURE:
<223> OTHER INFORMATION: Synthesized Primer

<400> SEQUENCE: 145
cgggcccgcc ttaac                                                  15

<210> SEQ ID NO 146
<211> LENGTH: 36
<212> TYPE: DNA
<213> ORGANISM: Artificial sequence
<220> FEATURE:
<223> OTHER INFORMATION: Synthesized Primer

<400> SEQUENCE: 146
gaaagtttta aataatttat attttcactc agagtt                           36

<210> SEQ ID NO 147
<211> LENGTH: 17
<212> TYPE: DNA
<213> ORGANISM: Artificial sequence
<220> FEATURE:

<223> OTHER INFORMATION: Synthesized Probe

<400> SEQUENCE: 147
cgcgcccgcc gaagaca                                                    17

<210> SEQ ID NO 148
<211> LENGTH: 15
<212> TYPE: DNA
<213> ORGANISM: Artificial sequence
<220> FEATURE:
<223> OTHER INFORMATION: Synthesized Primer

<400> SEQUENCE: 148
cgggcccgcc ttaac                                                      15

<210> SEQ ID NO 149
<211> LENGTH: 36
<212> TYPE: DNA
<213> ORGANISM: Artificial sequence
<220> FEATURE:
<223> OTHER INFORMATION: Synthesized Primer

<400> SEQUENCE: 149
gaaagtttta aataatttat attttcactc agagtt                               36

<210> SEQ ID NO 150
<211> LENGTH: 17
<212> TYPE: DNA
<213> ORGANISM: Artificial sequence
<220> FEATURE:
<223> OTHER INFORMATION: Synthesized Probe

<400> SEQUENCE: 150
cgcgcccgcc gaagaca                                                    17

<210> SEQ ID NO 151
<211> LENGTH: 15
<212> TYPE: DNA
<213> ORGANISM: Artificial sequence
<220> FEATURE:
<223> OTHER INFORMATION: Synthesized Primer

<400> SEQUENCE: 151
cgggcccgcc ttaac                                                      15

<210> SEQ ID NO 152
<211> LENGTH: 36
<212> TYPE: DNA
<213> ORGANISM: Artificial sequence
<220> FEATURE:
<223> OTHER INFORMATION: Synthesized Primer

<400> SEQUENCE: 152
gaaagtttta aataatttat attttcactc agagtt                               36

<210> SEQ ID NO 153
<211> LENGTH: 17
<212> TYPE: DNA
<213> ORGANISM: Artificial sequence
<220> FEATURE:
<223> OTHER INFORMATION: Synthesized Probe

<400> SEQUENCE: 153
cgcgcccgcc gaagaca                                                    17

<210> SEQ ID NO 154
<211> LENGTH: 17
<212> TYPE: DNA
<213> ORGANISM: Artificial sequence
<220> FEATURE:
<223> OTHER INFORMATION: Synthesized Primer

<400> SEQUENCE: 154
ggcgagcctg ccttttg                                                   17

<210> SEQ ID NO 155
<211> LENGTH: 32
<212> TYPE: DNA
<213> ORGANISM: Artificial sequence
<220> FEATURE:
<223> OTHER INFORMATION: Synthesized Primer

<400> SEQUENCE: 155
gatccgttgt tgaaagtttt aaataattta ta                                  32

<210> SEQ ID NO 156
<211> LENGTH: 31
<212> TYPE: DNA
<213> ORGANISM: Artificial sequence
<220> FEATURE:
<223> OTHER INFORMATION: Synthesized Probe

<400> SEQUENCE: 156
ctcgccgaag acaccttaga actctgtctg a                                   31

<210> SEQ ID NO 157
<211> LENGTH: 17
<212> TYPE: DNA
<213> ORGANISM: Artificial sequence
<220> FEATURE:
<223> OTHER INFORMATION: Synthesized Primer

<400> SEQUENCE: 157
ggcgagcctg ccttttg                                                   17

<210> SEQ ID NO 158
<211> LENGTH: 32
<212> TYPE: DNA
<213> ORGANISM: Artificial sequence
<220> FEATURE:
<223> OTHER INFORMATION: Synthesized Primer

<400> SEQUENCE: 158
gatccgttgt tgaaagtttt aaataattta ta                                  32

<210> SEQ ID NO 159
<211> LENGTH: 31
<212> TYPE: DNA
<213> ORGANISM: Artificial sequence
<220> FEATURE:
<223> OTHER INFORMATION: Synthesized Probe

<400> SEQUENCE: 159
ctcgccgaag acaccttaga actctgtctg a                                   31

<210> SEQ ID NO 160
<211> LENGTH: 19
<212> TYPE: DNA
<213> ORGANISM: Artificial sequence
<220> FEATURE:
<223> OTHER INFORMATION: Synthesized Primer

<400> SEQUENCE: 160
gcctgtccga gcgtcactt					19

<210> SEQ ID NO 161
<211> LENGTH: 15
<212> TYPE: DNA
<213> ORGANISM: Artificial sequence
<220> FEATURE:
<223> OTHER INFORMATION: Synthesized Primer

<400> SEQUENCE: 161
cccccgggat cggag					15

<210> SEQ ID NO 162
<211> LENGTH: 24
<212> TYPE: DNA
<213> ORGANISM: Artificial sequence
<220> FEATURE:
<223> OTHER INFORMATION: Synthesized Probe

<400> SEQUENCE: 162
ccaacacaca agccgtgctt gagg					24

<210> SEQ ID NO 163
<211> LENGTH: 17
<212> TYPE: DNA
<213> ORGANISM: Artificial sequence
<220> FEATURE:
<223> OTHER INFORMATION: Synthesized Primer

<400> SEQUENCE: 163
gtccaacctc ccaccca					17

<210> SEQ ID NO 164
<211> LENGTH: 25
<212> TYPE: DNA
<213> ORGANISM: Artificial sequence
<220> FEATURE:
<223> OTHER INFORMATION: Synthesized Primer

<400> SEQUENCE: 164
gctcagactg caatcttcag actgt					25

<210> SEQ ID NO 165
<211> LENGTH: 17
<212> TYPE: DNA
<213> ORGANISM: Artificial sequence
<220> FEATURE:
<223> OTHER INFORMATION: Synthesized Probe

<400> SEQUENCE: 165
ctgccctctg gcccgcg					17

<210> SEQ ID NO 166
<211> LENGTH: 21
<212> TYPE: DNA
<213> ORGANISM: Artificial sequence
<220> FEATURE:
<223> OTHER INFORMATION: Synthesized Primer

<400> SEQUENCE: 166
aggatcatta ctgagtgcgg a					21

<210> SEQ ID NO 167
<211> LENGTH: 20

```
<212> TYPE: DNA
<213> ORGANISM: Artificial sequence
<220> FEATURE:
<223> OTHER INFORMATION: Synthesized Primer

<400> SEQUENCE: 167
gccaaagcaa cagggtattc                                                    20

<210> SEQ ID NO 168
<211> LENGTH: 20
<212> TYPE: DNA
<213> ORGANISM: Artificial sequence
<220> FEATURE:
<223> OTHER INFORMATION: Synthesized Probe

<400> SEQUENCE: 168
ccctcgcggg tccaacctcc                                                    20

<210> SEQ ID NO 169
<211> LENGTH: 20
<212> TYPE: DNA
<213> ORGANISM: Artificial sequence
<220> FEATURE:
<223> OTHER INFORMATION: Synthesized Primer

<400> SEQUENCE: 169
ttaccgagtg cgggttctaa                                                    20

<210> SEQ ID NO 170
<211> LENGTH: 17
<212> TYPE: DNA
<213> ORGANISM: Artificial sequence
<220> FEATURE:
<223> OTHER INFORMATION: Synthesized Primer

<400> SEQUENCE: 170
cgaggcaacg cggtaac                                                       17

<210> SEQ ID NO 171
<211> LENGTH: 17
<212> TYPE: DNA
<213> ORGANISM: Artificial sequence
<220> FEATURE:
<223> OTHER INFORMATION: Synthesized Probe

<400> SEQUENCE: 171
ccaacctccc acccgtg                                                       17

<210> SEQ ID NO 172
<211> LENGTH: 22
<212> TYPE: DNA
<213> ORGANISM: Artificial sequence
<220> FEATURE:
<223> OTHER INFORMATION: Synthesized Primer

<400> SEQUENCE: 172
cattactgag tgagggccct ct                                                 22

<210> SEQ ID NO 173
<211> LENGTH: 15
<212> TYPE: DNA
<213> ORGANISM: Artificial sequence
<220> FEATURE:
<223> OTHER INFORMATION: Synthesized Primer

<400> SEQUENCE: 173
```

```
cgtgaggcgg gagca                                                    15

<210> SEQ ID NO 174
<211> LENGTH: 17
<212> TYPE: DNA
<213> ORGANISM: Artificial sequence
<220> FEATURE:
<223> OTHER INFORMATION: Synthesized Probe

<400> SEQUENCE: 174
ccaacctccc acccgtg                                                  17

<210> SEQ ID NO 175
<211> LENGTH: 22
<212> TYPE: DNA
<213> ORGANISM: Artificial sequence
<220> FEATURE:
<223> OTHER INFORMATION: Synthesized Primer

<400> SEQUENCE: 175
cattactgag tgagggccct ct                                            22

<210> SEQ ID NO 176
<211> LENGTH: 15
<212> TYPE: DNA
<213> ORGANISM: Artificial sequence
<220> FEATURE:
<223> OTHER INFORMATION: Synthesized Primer

<400> SEQUENCE: 176
cgtgaggcgg gagca                                                    15

<210> SEQ ID NO 177
<211> LENGTH: 17
<212> TYPE: DNA
<213> ORGANISM: Artificial sequence
<220> FEATURE:
<223> OTHER INFORMATION: Synthesized Probe

<400> SEQUENCE: 177
ccaacctccc acccgtg                                                  17

<210> SEQ ID NO 178
<211> LENGTH: 22
<212> TYPE: DNA
<213> ORGANISM: Artificial sequence
<220> FEATURE:
<223> OTHER INFORMATION: Synthesized Primer

<400> SEQUENCE: 178
cattactgag tgagggccct ct                                            22

<210> SEQ ID NO 179
<211> LENGTH: 15
<212> TYPE: DNA
<213> ORGANISM: Artificial sequence
<220> FEATURE:
<223> OTHER INFORMATION: Synthesized Primer

<400> SEQUENCE: 179
cgtgaggcgg gagca                                                    15

<210> SEQ ID NO 180
<211> LENGTH: 17
<212> TYPE: DNA
<213> ORGANISM: Artificial sequence
```

```
<220> FEATURE:
<223> OTHER INFORMATION: Synthesized Probe

<400> SEQUENCE: 180
ccaacctccc acccgtg                                                    17

<210> SEQ ID NO 181
<211> LENGTH: 22
<212> TYPE: DNA
<213> ORGANISM: Artificial sequence
<220> FEATURE:
<223> OTHER INFORMATION: Synthesized Primer

<400> SEQUENCE: 181
cattactgag tgagggccct ct                                              22

<210> SEQ ID NO 182
<211> LENGTH: 15
<212> TYPE: DNA
<213> ORGANISM: Artificial sequence
<220> FEATURE:
<223> OTHER INFORMATION: Synthesized Primer

<400> SEQUENCE: 182
cgtgaggcgg gagca                                                      15

<210> SEQ ID NO 183
<211> LENGTH: 17
<212> TYPE: DNA
<213> ORGANISM: Artificial sequence
<220> FEATURE:
<223> OTHER INFORMATION: Synthesized Probe

<400> SEQUENCE: 183
ccaacctccc acccgtg                                                    17

<210> SEQ ID NO 184
<211> LENGTH: 22
<212> TYPE: DNA
<213> ORGANISM: Artificial sequence
<220> FEATURE:
<223> OTHER INFORMATION: Synthesized Primer

<400> SEQUENCE: 184
cattactgag tgagggccct ct                                              22

<210> SEQ ID NO 185
<211> LENGTH: 15
<212> TYPE: DNA
<213> ORGANISM: Artificial sequence
<220> FEATURE:
<223> OTHER INFORMATION: Synthesized Primer

<400> SEQUENCE: 185
cgtgaggcgg gagca                                                      15

<210> SEQ ID NO 186
<211> LENGTH: 17
<212> TYPE: DNA
<213> ORGANISM: Artificial sequence
<220> FEATURE:
<223> OTHER INFORMATION: Synthesized Probe

<400> SEQUENCE: 186
ccaacctccc acccgtg                                                    17
```

```
<210> SEQ ID NO 187
<211> LENGTH: 16
<212> TYPE: DNA
<213> ORGANISM: Artificial sequence
<220> FEATURE:
<223> OTHER INFORMATION: Synthesized Primer

<400> SEQUENCE: 187
caccgcccgt cgctac                                                      16

<210> SEQ ID NO 188
<211> LENGTH: 27
<212> TYPE: DNA
<213> ORGANISM: Artificial sequence
<220> FEATURE:
<223> OTHER INFORMATION: Synthesized Primer

<400> SEQUENCE: 188
gcttagtttg ccatagttct ctaacaa                                          27

<210> SEQ ID NO 189
<211> LENGTH: 33
<212> TYPE: DNA
<213> ORGANISM: Artificial sequence
<220> FEATURE:
<223> OTHER INFORMATION: Synthesized Probe

<400> SEQUENCE: 189
ccgattgaat ggttatagtg agcatatggg atc                                   33

<210> SEQ ID NO 190
<211> LENGTH: 23
<212> TYPE: DNA
<213> ORGANISM: Artificial sequence
<220> FEATURE:
<223> OTHER INFORMATION: Synthesized Primer

<400> SEQUENCE: 190
cccctgcgta gtagatccta cat                                              23

<210> SEQ ID NO 191
<211> LENGTH: 22
<212> TYPE: DNA
<213> ORGANISM: Artificial sequence
<220> FEATURE:
<223> OTHER INFORMATION: Synthesized Primer

<400> SEQUENCE: 191
tccgaggtca aaccatgaaa ta                                               22

<210> SEQ ID NO 192
<211> LENGTH: 18
<212> TYPE: DNA
<213> ORGANISM: Artificial sequence
<220> FEATURE:
<223> OTHER INFORMATION: Synthesized Probe

<400> SEQUENCE: 192
tcgcatcggg tcccggcg                                                    18

<210> SEQ ID NO 193
<211> LENGTH: 23
<212> TYPE: DNA
<213> ORGANISM: Artificial sequence
<220> FEATURE:
<223> OTHER INFORMATION: Synthesized Primer
```

<400> SEQUENCE: 193 ccccctgcgta gtagatccta cat                                              23

<210> SEQ ID NO 194
<211> LENGTH: 22
<212> TYPE: DNA
<213> ORGANISM: Artificial sequence
<220> FEATURE:
<223> OTHER INFORMATION: Synthesized Primer

<400> SEQUENCE: 194
tccgaggtca aaccatgaaa ta                                                22

<210> SEQ ID NO 195
<211> LENGTH: 18
<212> TYPE: DNA
<213> ORGANISM: Artificial sequence
<220> FEATURE:
<223> OTHER INFORMATION: Synthesized Probe

<400> SEQUENCE: 195
tcgcatcggg tcccggcg                                                     18

<210> SEQ ID NO 196
<211> LENGTH: 21
<212> TYPE: DNA
<213> ORGANISM: Artificial sequence
<220> FEATURE:
<223> OTHER INFORMATION: Synthesized Primer

<400> SEQUENCE: 196 cccccctgcgt agtagtaaag c                                                21

<210> SEQ ID NO 197
<211> LENGTH: 20
<212> TYPE: DNA
<213> ORGANISM: Artificial sequence
<220> FEATURE:
<223> OTHER INFORMATION: Synthesized Primer

<400> SEQUENCE: 197
tccgaggtca aaccatcaag                                                   20

<210> SEQ ID NO 198
<211> LENGTH: 18
<212> TYPE: DNA
<213> ORGANISM: Artificial sequence
<220> FEATURE:
<223> OTHER INFORMATION: Synthesized Probe

<400> SEQUENCE: 198
tcgcatcggg tcccggcg                                                     18

<210> SEQ ID NO 199
<211> LENGTH: 21
<212> TYPE: DNA
<213> ORGANISM: Artificial sequence
<220> FEATURE:
<223> OTHER INFORMATION: Synthesized Primer

<400> SEQUENCE: 199
tcccaaaccc ttatgtgaac c                                                 21

<210> SEQ ID NO 200

```
<211> LENGTH: 25
<212> TYPE: DNA
<213> ORGANISM: Artificial sequence
<220> FEATURE:
<223> OTHER INFORMATION: Synthesized Primer

<400> SEQUENCE: 200
gtttgccact cagagaatac tgaaa                                            25

<210> SEQ ID NO 201
<211> LENGTH: 18
<212> TYPE: DNA
<213> ORGANISM: Artificial sequence
<220> FEATURE:
<223> OTHER INFORMATION: Synthesized Probe

<400> SEQUENCE: 201
ctgcgcccgg atccaggc                                                    18

<210> SEQ ID NO 202
<211> LENGTH: 20
<212> TYPE: DNA
<213> ORGANISM: Artificial sequence
<220> FEATURE:
<223> OTHER INFORMATION: Synthesized Primer

<400> SEQUENCE: 202
cccaaaccca atgtgaacca                                                  20

<210> SEQ ID NO 203
<211> LENGTH: 18
<212> TYPE: DNA
<213> ORGANISM: Artificial sequence
<220> FEATURE:
<223> OTHER INFORMATION: Synthesized Primer

<400> SEQUENCE: 203
tccgcgaggg gactacag                                                    18

<210> SEQ ID NO 204
<211> LENGTH: 20
<212> TYPE: DNA
<213> ORGANISM: Artificial sequence
<220> FEATURE:
<223> OTHER INFORMATION: Synthesized Probe

<400> SEQUENCE: 204
cccaaaccca atgtgaacca                                                  20

<210> SEQ ID NO 205
<211> LENGTH: 20
<212> TYPE: DNA
<213> ORGANISM: Artificial sequence
<220> FEATURE:
<223> OTHER INFORMATION: Synthesized Primer

<400> SEQUENCE: 205
cccaaaccca atgtgaacca                                                  20

<210> SEQ ID NO 206
<211> LENGTH: 18
<212> TYPE: DNA
<213> ORGANISM: Artificial sequence
<220> FEATURE:
<223> OTHER INFORMATION: Synthesized Primer

<400> SEQUENCE: 206
```
tccgcgaggg gactacag                                         18

<210> SEQ ID NO 207
<211> LENGTH: 20
<212> TYPE: DNA
<213> ORGANISM: Artificial sequence
<220> FEATURE:
<223> OTHER INFORMATION: Synthesized Probe

<400> SEQUENCE: 207
cccaaaccca atgtgaacca                                       20

<210> SEQ ID NO 208
<211> LENGTH: 20
<212> TYPE: DNA
<213> ORGANISM: Artificial sequence
<220> FEATURE:
<223> OTHER INFORMATION: Synthesized Primer

<400> SEQUENCE: 208
cccaaaccca atgtgaacca                                       20

<210> SEQ ID NO 209
<211> LENGTH: 18
<212> TYPE: DNA
<213> ORGANISM: Artificial sequence
<220> FEATURE:
<223> OTHER INFORMATION: Synthesized Primer

<400> SEQUENCE: 209
tccgcgaggg gactacag                                         18

<210> SEQ ID NO 210
<211> LENGTH: 20
<212> TYPE: DNA
<213> ORGANISM: Artificial sequence
<220> FEATURE:
<223> OTHER INFORMATION: Synthesized Probe

<400> SEQUENCE: 210
cccaaaccca atgtgaacca                                       20

<210> SEQ ID NO 211
<211> LENGTH: 21
<212> TYPE: DNA
<213> ORGANISM: Artificial sequence
<220> FEATURE:
<223> OTHER INFORMATION: Synthesized Primer

<400> SEQUENCE: 211
ggcttagtga atccttcgga g                                     21

<210> SEQ ID NO 212
<211> LENGTH: 22
<212> TYPE: DNA
<213> ORGANISM: Artificial sequence
<220> FEATURE:
<223> OTHER INFORMATION: Synthesized Primer

<400> SEQUENCE: 212
gtttacccaa ctttgcagtc ca                                    22

<210> SEQ ID NO 213
<211> LENGTH: 23
<212> TYPE: DNA

```
<213> ORGANISM: Artificial sequence
<220> FEATURE:
<223> OTHER INFORMATION: Synthesized Probe

<400> SEQUENCE: 213
tgtgccgttg ccggctcaaa tag                                            23

<210> SEQ ID NO 214
<211> LENGTH: 27
<212> TYPE: DNA
<213> ORGANISM: Artificial sequence
<220> FEATURE:
<223> OTHER INFORMATION: Synthesized Primer

<400> SEQUENCE: 214
gatatttctt gtgaattgca gaagtga                                        27

<210> SEQ ID NO 215
<211> LENGTH: 26
<212> TYPE: DNA
<213> ORGANISM: Artificial sequence
<220> FEATURE:
<223> OTHER INFORMATION: Synthesized Primer

<400> SEQUENCE: 215
ttgattcgaa attttagaag agcaaa                                         26

<210> SEQ ID NO 216
<211> LENGTH: 32
<212> TYPE: DNA
<213> ORGANISM: Artificial sequence
<220> FEATURE:
<223> OTHER INFORMATION: Synthesized Probe

<400> SEQUENCE: 216
caattccaag agagaaacaa cgctcaaaca ag                                  32
```